(12) United States Patent
Addison et al.

(10) Patent No.: US 11,026,586 B2
(45) Date of Patent: Jun. 8, 2021

(54) DETERMINING CHANGES TO AUTOREGULATION

(71) Applicant: Covidien LP, Mansfield, MA (US)

(72) Inventors: Paul S. Addison, Edinburgh (GB);
Dean Montgomery, Edinburgh (GB);
James N. Watson, Edinburgh (GB)

(73) Assignee: Covidien LP, Mansfield, MA (US)

( * ) Notice: Subject to any disclaimer, the term of this patent is extended or adjusted under 35 U.S.C. 154(b) by 635 days.

(21) Appl. No.: 15/962,438

(22) Filed: Apr. 25, 2018

(65) Prior Publication Data

US 2019/0328241 A1   Oct. 31, 2019

(51) Int. Cl.
*A61B 5/0205* (2006.01)
*A61B 5/021* (2006.01)
(Continued)

(52) U.S. Cl.
CPC ............ *A61B 5/0205* (2013.01); *A61B 5/021* (2013.01); *A61B 5/0295* (2013.01);
(Continued)

(58) Field of Classification Search
CPC ......... A61B 5/0205; A61B 5/00; A61B 5/021; A61B 5/0295; A61B 5/1455; A61B 5/742;
(Continued)

(56) References Cited

U.S. PATENT DOCUMENTS 4,688,577 A    8/1987   Bro
5,579,774 A   12/1996   Miller et al.
(Continued)

FOREIGN PATENT DOCUMENTS

CN   100399990 A   12/2006
DE   10331027 A1    1/2005
(Continued)

OTHER PUBLICATIONS

Chuan et al., "Is cerebrovascular autoregulation associated with outcomes after major noncardiac surgery? A prospective observational pilot study," Acta Anaesthesiol Scand., Aug. 5, 2018, 10 pp.
(Continued)

*Primary Examiner* — Eric J Messersmith
(74) *Attorney, Agent, or Firm* — Shumaker & Sieffert, P.A.

(57) ABSTRACT

In some examples, a device includes processing circuitry configured to receive first and second signals indicative of first and second physiological parameters, respectively, of a patient. The processing circuitry is also configured to determine a first estimate of a limit of autoregulation of the patient based on the first and second signals. The processing circuitry is further configured to determine a difference between the first estimate of the limit of autoregulation and one or more other estimates of the limit of autoregulation. The processing circuitry is configured to determine a weighted average of the first estimate and a previous value of the limit of autoregulation based on the difference between the first estimate and the one or more other estimates. The processing circuitry is configured to determine an autoregulation status based on the weighted average and output, for display via the display, an indication of the autoregulation status.

20 Claims, 8 Drawing Sheets

(51) Int. Cl.
  *A61B 5/0295* (2006.01)
  *A61B 5/00* (2006.01)
  *A61B 5/1455* (2006.01)
  *A61B 5/024* (2006.01)
(52) U.S. Cl.
  CPC ........ *A61B 5/14551* (2013.01); *A61B 5/7246* (2013.01); *A61B 5/7278* (2013.01); *A61B 5/742* (2013.01); *A61B 5/02416* (2013.01)
(58) Field of Classification Search
  CPC . A61B 5/14551; A61B 5/7246; A61B 5/4064; A61B 5/7278; A61B 5/029
  See application file for complete search history.

(56) References Cited

U.S. PATENT DOCUMENTS

| | | | |
|---|---|---|---|
| 6,438,399 | B1 | 8/2002 | Kurth |
| 6,599,251 | B2 | 7/2003 | Chen et al. |
| 6,875,176 | B2 | 4/2005 | Mourad et al. |
| 7,532,919 | B2 | 5/2009 | Soyemi et al. |
| 7,744,541 | B2 | 6/2010 | Baruch et al. |
| 7,998,075 | B2 | 8/2011 | Ragauskas et al. |
| 8,057,398 | B2 | 11/2011 | Mcnames et al. |
| 8,062,224 | B2 | 11/2011 | Ragauskas et al. |
| 8,211,022 | B2 | 7/2012 | Lo et al. |
| 8,366,627 | B2 | 2/2013 | Kashif et al. |
| 8,433,384 | B2 | 4/2013 | Bechtel et al. |
| 8,512,260 | B2 | 8/2013 | Grudic et al. |
| 8,556,811 | B2 | 10/2013 | Brady |
| 8,852,094 | B2 | 10/2014 | Al-ali et al. |
| 9,192,330 | B2 | 11/2015 | Lin et al. |
| 9,861,317 | B2 | 1/2018 | Ochs |
| 2002/0099295 | A1 | 7/2002 | Gil et al. |
| 2003/0219797 | A1 | 11/2003 | Zhao et al. |
| 2009/0326386 | A1 | 12/2009 | Sethi et al. |
| 2010/0030054 | A1 | 2/2010 | Baruch et al. |
| 2011/0105912 | A1* | 5/2011 | Widman ............... A61B 5/021 600/483 |
| 2012/0004517 | A1 | 1/2012 | Starr et al. |
| 2012/0130697 | A1* | 5/2012 | Woodford ............. G16H 40/60 703/11 |
| 2012/0253211 | A1 | 10/2012 | Brady et al. |
| 2013/0144140 | A1 | 6/2013 | Frederick et al. |
| 2013/0190632 | A1 | 7/2013 | Baruch et al. |
| 2014/0073888 | A1 | 3/2014 | Kim |
| 2014/0278285 | A1 | 9/2014 | Marmarelis et al. |
| 2015/0230758 | A1 | 8/2015 | Ochs |
| 2016/0081563 | A1 | 3/2016 | Wiard et al. |
| 2016/0106372 | A1 | 4/2016 | Addison et al. |
| 2016/0162786 | A1 | 6/2016 | Grudic et al. |
| 2016/0220115 | A1 | 8/2016 | Fisher et al. |
| 2016/0324425 | A1 | 11/2016 | Addison et al. |
| 2016/0367197 | A1 | 12/2016 | Addison et al. |
| 2017/0105631 | A1 | 4/2017 | Addison et al. |
| 2018/0014791 | A1 | 1/2018 | Montgomery et al. |

FOREIGN PATENT DOCUMENTS

| | | |
|---|---|---|
| RU | 2465829 C1 | 11/2012 |
| WO | WO 2016015057 A1 | 1/2016 |

OTHER PUBLICATIONS

Ameloot et al., "An observational near-infrared spectroscopy study on cerebral autoregulation in post-cardiac arrest patients: Time to drop 'one-size-fits-all' hemodynamic targets?," Resuscitation 90, 121-126, Jan. 2015.
Brady, MD, et al., "Monitoring Cerebrovascular Autoregulation Refining care goals in the ICU," Apr. 21, 2009, 15 pp.
Brady, MD et al., "Real-time continuous monitoring of cerebral blood flow autoregulation using near-infrared spectroscopy in patients undergoing cardiopulmonary bypass," Stroke 41, pp. 1951-1956, Feb. 2010.
Brady, MD et al., "A Dynamic Association Between Cavopulmonary Shunt Pressure and Cerebrovascular Autoregulation in an Infant With Congenital Heart Disease and Intracranial Hemorrhage," J. Cardiothorac. Vasc. Anesth. Vo. 23, No. 2, pp. 215-218; Apr. 2009.
Brady, MD et al., "Continuous Measurement of Autoregulation by Spontaneous Fluctuations in Cerebral Perfusion Pressure: Comparison of 3 Methods," Stroke. 39, pp. 2531-2537; Sep. 2008.
Brady, MD et al., "Continuous Monitoring of Cerebrovascular Pressure Reactivity After Traumatic Brain Injury in Children," Pediatrics 124, e1205-e1212, Dec. 2009.
Brady, MD et al., "Continuous Time-Domain Analysis of Cerebrovascular Autoregulation Using Near-infrared Spectroscopy," Stroke 38, pp. 2818-2825; Oct. 2007.
Brady, MD et al., "Monitoring Cerebral Blood Flow Pressure Autoregulation in Pediatric Patients During Cardiac Surgery," Stroke 41, 1957-1962, Sep. 2010.
Brady, MD et al., "Noninvasive Autoregulation Monitoring With and Without Intracranial Pressure in the Naïve Piglet Brain," Anesth. Analg. vol. 111, No. 1, 191-195; Jul. 2010.
Budohoski, MD et al., "Bilateral Failure of Cerebral Autoregulation is Related to Unfavorable Outcome After Subarachnoid Hemorrhage," Neurocrit. Care 22, 65-73, Jul. 2014.
Budohoski, MD, et al., "The Relationship Between Cerebral Blood Flow Autoregulation and Cerebrovascular Pressure Reactivity After Traumatic Brain Injury," Neurosurgery 71, pp. 652-660 May 2012.
Calviere et al., "Prediction of Delayed Cerebral Ischemia After Subarachnoid Hemorrhage Using Cerebral Blood Flow Velocities and Cerebral Autoregulation Assessment," Neurocrit. Care, Feb. 2015.
Czosnyka, PhD, et al., "Intracranial pressure: More Than a Number," Neurosurg. Focus 22, E10, May 2007.
Czosnyka, PhD, et al., "Monitoring of Cerebrovascular Autoregulation: Facts, myths, and missing links," Neurocrit. Care 10, 373-386, Jan. 2009.
Czosnyka, PhD, et al., "Monitoring of Cerebral Autoregulation in Head-Injured Patients," Stroke. 27, 1829-1834, Oct. 1996.
Depreitere et al., "Pressure autoregulation monitoring and cerebral perfusion pressure target recommendation in patients with severe traumatic brain injury based on minute-by-minute monitoring data," J. Neurosurg. 120, pp. 1451-1457, Apr. 2014.
Dias et al., "Kidney-Brain Link in Traumatic Brain Injury Patients? A preliminary report," Neurocrit. Care, Oct. 2014, 12 pp.
Dias et al., "Optimal Cerebral Perfusion Pressure Management at Bedside: A Single-Center Pilot Study," Neurocrit. Care, Jan. 2015, 13 pp.
Diedler, MD et al., "The Limitations of Near-Infrared Spectroscopy to Assess CerebrovascularR: The Role of Slow Frequency Oscillations," Anesth. Analg. vol. 113 No. 4, pp. 849-857, Oct. 2011.
Donnelly et al., "Further understanding of cerebral autoregulation at the bedside: possible implications for future therapy," Expert Rev. Neurother. 15, pp. 169-185, Jan. 2015.
Eide, MD, PhD., et al. "Pressure-derived versus pressure wave amplitude—derived indices of cerebrovascular pressure reactivity in relation to early clinical state and 12-month outcome following aneurysmal subarachnoid hemorrhage," J. Neurosurg. 116, pp. 961-971, May 2012.
Gilmore et al., "Relationship between cerebrovascular dysautoregulation and arterial blood pressure in the premature infant," J. Perinatol. 31, pp. 722-729, Mar. 2011.
Hori et al., "Effect of carotid revascularization on cerebral autoregulation in combined cardiac surgery," Eur. J. Cardio-Thoracic Surg., Feb. 2015, 7 pp.
Howells et al., "An optimal frequency range for assessing the pressure reactivity index in patients with traumatic brain injury," J. Clin. Monit. Comput., pp. 97-105, Mar. 2014.
Howlett et al., "Cerebrovascular autoregulation and neurologic injury in neonatal hypoxic-ischemic encephalopathy," Pediatr. Res. vol. 74, No. 5, pp. 525-535, Nov. 2013.
Jaeger, MD et al., "Effects of cerebrovascular pressure reactivity-guided optimization of cerebral perfusion pressure on brain tissue oxygenation after traumatic brain injury," Crit. Care Med. vol. 38, No. 5, pp. 1343-1347, May 2010.

(56) References Cited

OTHER PUBLICATIONS

Jaeger, MD, et al., "Continuous monitoring of cerebrovascular autoregulation after subarachnoid hemorrhage by brain tissue oxygen pressure reactivity and its relation to delayed cerebral infarction," Stroke 38, pp. 981-986, Apr.-May 2007.
Kvandal et al., "Impaired cerebrovascular reactivity after acute traumatic brain injury can be detected by wavelet phase coherence analysis of the intracranial and arterial blood pressure signals," J. Clin. Monit. Comput. 27, pp. 375-383, May 2013.
Laflam et al., "Shoulder Surgery in the Beach Chair Position Is Associated with Diminished Cerebral Autoregulation but No Differences in Postoperative Cognition or Brain Injury Biomarker Levels Compared with Supine Positioning," Anesth. Analg. vol. 120, No. 1, pp. 176-185, Jan. 2015.
Lang MD, PhD, et al., "A Review of Cerebral Autoregulation: Assessment and Measurements," Aust. Anaesth. 161-172, 2005, (Applicant points out, in accordance with MPEP 609.04(a), that the year of publication, 2005, is sufficiently earlier than the effective U.S. filing date, Mar. 5, 2018, so that the particular month of publication is not in issue.).
Lang et al., "Short pressure reactivity index versus long pressure reactivity index in the management of traumatic brain injury," J. Neurosurg. vol. 122, pp. 588-594, Mar. 2015.
Lang et al., "Continuous monitoring of cerebrovascular autoregulation: a validation study," J. Neurol. Neurosurg. Psychiatry 72, pp. 583-586, Jan. 2002.
Lee et al., "A pilot study of cerebrovascular reactivity autoregulation after pediatric cardiac arrest," Resuscitation 85, pp. 1387-1393, Jun. 2014.
Lee, J. K. et al., "Cerebral blood flow and cerebrovascular autoregulation in a swine model of pediatric cardiac arrest and hypothermia*," Crit. Care Med. vol. 39, No. 10, pp. 2337-2345, Oct. 2011.
Lee, MD et al., "Cerebrovascular Reactivity Measured by Near-Infrared Spectroscopy," Stroke 40, pp. 1820-1826, Oct. 2009.
Lee, MD, et al., "Noninvasive autoregulation monitoring in a swine model of pediatric cardiac arrest," Anesth. Analg. vol. 114, pp. 825-836, Apr. 2012.
Lewis et al., "Continuous Correlation Between Intracranial Pressure and Cerebral Blood Flow Velocity Reflects Cerebral Autoregulation Impairment During Intracranial Pressure Plateau Waves," Neurocrit. Care 21, pp. 514-525, May 2014.
Liu et al., "Comparison of frequency and time domain methods of assessment of cerebral autoregulation in traumatic brain injury," J. Cereb. Blood Flow Metab. 35, pp. 248-256, Nov. 2014.
Nasr et al., "Baroreflex and Cerebral Autoregulation Are Inversely Correlated," Circ. J. vol. 78, pp. 2460-2467, Oct. 2014.
Nasr et al., "Cerebral autoregulation in patients with obstructive sleep apnea syndrome during wakefulness," Eur. J. Neurol. 16, pp. 386-391, Mar. 2009.
Ono, MD et al., "Blood pressure excursions below the cerebral autoregulation threshold during cardiac surgery are associated with acute kidney injury," Crit. Care Med. 41, pp. 464-471, Feb. 2013.
Ono, MD et al., "Cerebral Blood Flow Autoregulation Is Preserved After Hypothermic Circulatory Arrest," Ann. Thorac. Surg. 96, pp. 2045-2053, Dec. 2013.
Ono, MD et al., "Duration and magnitude of blood pressure below cerebral autoregulation threshold during cardiopulmonary bypass is associated with major morbidity and operative mortality," J. Thorac. Cardiovasc. Surg. 147, pp. 483-489, Jan. 2014.
Ono, MD et al., "Risks for impaired cerebral autoregulation during cardiopulmonary bypass and postoperative stroke," Br. J. Anaesth. 109, pp. 391-398, Jun. 2012.
Ono, MD et al., "Validation of a Stand-Alone Near-Infrared Spectroscopy System for Monitoring Cerebral Autoregulation During Cardiac Surgery," Anesth. Analg. vol. 116, No. 1, pp. 198-204, Jan. 2013.
Papademetriou et al., "Multichannel near infrared spectroscopy indicates regional variations in cerebral autoregulation in infants supported on extracorporeal membrane oxygenation," J. Biomed. Opt., vol. 17, pp. 067008-1-067008-9, Jun. 2012.

Radolovich et al., "Pulsatile Intracranial Pressure and Cerebral Autoregulation After Traumatic Brain Injury," Neurocrit. Care 15, pp. 379-386, Dec. 2011.
Radolovich et al., "Reactivity of Brain Tissue Oxygen to Change in Cerebral Perfusion Pressure in Head Injured Patients, " Neurocrit. Care 10, pp. 274-279, Feb. 2009.
Reinhard, MD et al., "Cerebral Autoregulation in Carotid Artery Occlusive Disease Assessed From Spontaneous Blood Pressure Fluctuations by the Correlation Coefficient Index," Stroke 34, pp. 2138-2144, May 2003.
Reinhard, MD et al., "Cerebral dysautoregulation and the risk of ischemic events in occlusive carotid artery disease," J. Neurol. 255, pp. 1182-1189, Jun. 2008.
Schmidt et al., "Impaired autoregulation is associated with mortality in severe cerebral diseases" Clinical Neurosciences and Mental Health, 1 (Suppl. 1), May 2014, 6 pp.
Schmidt et al., "Asymmetry of cerebral autoregulation does not correspond to asymmetry of cerebrovascular pressure reactivity," Perspect. Med. 1-12, pp. 285-289, Sep. 2012.
Schmidt et al., "Cerebral Autoregulatory Response Depends on the Direction of Change in Perfusion Pressure," J. Neurotrauma 26, pp. 651-656, May 2009.
Severdija et al., "Assessment of dynamic cerebral autoregulation and cerebral carbon dioxide reactivity during normothermic cardiopulmonary bypass," Med. Biol. Eng. Comput. 53, pp. 195-203, Nov. 2014.
Smith, "Shedding light on the adult brain: a review of the clinical applications of near-infrared spectroscopy," Philos. Trans. R. Soc. A Math. Phys. Eng. Sci. 369, pp. 4452-4469 Oct. 2011.
Soul et al., "Fluctuating Pressure-Passivity Is Common in the Cerebral Circulation of Sick Premature Infants," Pediatric Research 61, No. 4, Nov. 2007, pp. 467-473.
Steiner, MD et al., "Continuous monitoring of cerebrovascular pressure reactivity allows determination of optimal cerebral perfusion pressure in patients with traumatic brain injury," Crit. Care Med. 30, pp. 733-738, Apr. 2002.
Steiner et al., "Near-Infrared Spectroscopy Can Monitor Dynamic Cerebral Autoregulation in Adults," Neurocrit. Care 10, pp. 122-128, Sep. 2008.
Tekes et al., "Apparent Diffusion Coefficient Scalars Correlate with Near-Infrared Spectroscopy Markers of Cerebrovascular Autoregulation in Neonates Cooled for Perinatal Hypoxic-Ischemic Injury," Am. J. Neuroradiol. 36, pp. 188-193, Jan. 2015.
Zheng et al., "Continuous Cerebral Blood Flow Autoregulation Monitoring in Patients Undergoing Liver Transplantation," Neurocrit. Care 17, pp. 77-84, Aug. 2012.
Zweifel et al., "Continuous Assessment of Cerebral Autoregulation With Near-Infrared Spectroscopy in Adults After Subarachnoid Hemorrhage," Stroke 41, pp. 1963-1968, Jan. 2010.
Zweifel et al., "Continuous time-domain monitoring of cerebral autoregulation in neurocritical care," Med. Eng. Phys. 36, 638-645, Feb. 2014.
Tsalach et al., "Cerebral Autoregulation Real-Time Monitoring," PLOS One, Aug. 29, 2016, 14 pp.
Chung MD, PhD et al., "Assessment of Noninvasive Regional Brain Oximetry in Posterior Reversible Encephalopahty Syndrome and Reversible Cerebral Vasoconstriction Syndrome," Journal of Intensive Care Medicine, vol. 31(6), Jan. 2016, pp. 415-419.
Lee et al., "Cerebrovascular Autoregulation in pediatric moyamoya Disease" Pediatric Anesthesia, 23, pp. 547-556, Jun. 2013.
Steppan, MD, et al., "Cerebral and Tissue Oximetryc" Best Pract Res Clin Anaesthesiol, Dec. 2014, pp. 429-439.
Brady et al., "A New Monitor of Pressure Autoregulation: What Does It Add?" International Anesthesia Research Society, Nov. 2015, vol. 121, No. 5, pp. 1121-1123.
Prabhakar et al., "Current concepts of optimal cerebral perfusion pressure in traumatic brain injury," J. Anaesthesiol Clin Pharmacol, Jul.-Sep. 2014, pp. 318-327.
Lang et al., "Continuous monitoring of cerebrovascular autoregulation: a validation study," J Neurol Neurosurg Psychiatry, pp. 583-586, Jan. 2002.

(56) References Cited

OTHER PUBLICATIONS

Lazaridis et al., Optimal cerebral perfusion pressure: are we ready for it? Neurological Research, vol. 35, No. 2, Nov. 12, 2013, pp. 138-148.
Joshi et al., "Predicting the Limits of Cerebral Autoregulation During Cardiopulmonary Bypass," Anesthesia-Analgesia, Mar. 2012, vol. 114, No. 3, pp. 503-510.
Olsen et al., "Validation of Transcranial Near-Infrared Spectroscopy for Evaluation of Cerebral Blood Flow Autoregulation," Journal of Neurosurgical Anesthesiology, pp. 280-285, Oct. 1996.
Addison et al., "Gradient adjustment method for better discriminating correlating and non-correlating regions of physiological signals: application to the partitioning of impaired and intact zones of cerebral autoregulation," J Clin Moit Comput, Aug. 2016, 11 pp.
Montgomery et al., "Data clustering methods for the determination of cerebral autoregulation functionality," J Clin Monit Comput, Sep. 2015, 8 pp.
Brady et al., "The Lower Limit of Cerebral Blood Flow Autoregulation is Increased with Elevated Intracranial Pressure," vol. 108, No. 4, Apr. 2009.
Gao et al., "Mathematical considerations for modeling cerebral blood flow autoregulation to systemic arterial pressure," accessed on Sep. 19, 2016, accessed from http://ajpheart.physiology.org/., pp. H1023-H1031.
Hauerberg et al., "The Upper Limit of Cerebral Blood Flow Autoregulation in Acute Intracranial Hypertension," Journal of Neurosurgical Anesthesiology, vol. 10, No. 2, pp. 106-112, May 1998.
Hori et al., "Arterial pressure above the upper cerebral autoregulation limit during cardiopulmonary bypass is associated with postoperative delirium," British Journal of Anaesthesia Sep. 2014, pp. 1009-1017.
Kamar et al., "Detecting Cerebral Autoregulation Thresholds Using a Noninvasive Cerebral Flow Monitor," Ornim medical, May 2013, Portugal Poster, 1 pp.
Lucas et al., "Influence of Changes in Blood Pressure on cerebral Perfusion and Oxygenation," Hypertension, Oct. 2009, pp. 698-705.
Minassian et al., "Changes in intracranial pressure and cerebral autoregulation in patients with severe traumatic brain injury," vol. 30, Jul. 2002, pp. 1616-1622.
Pesek, MD, et al., "The upper limit of cerebral blood flow autoregulation is decreased with elevations in intracranial pressure," Neurosurgery, vol. 75, No. 2, Aug. 2014, pp. 163-170.
Sadoshima et al., "Upper Limit of Cerebral Autoregulation During Development of Hypertension in Spontaneously Hypertensive Rats—Effect of Sympathetic Denervation," vol. 16, No. 3, May-Jun. 1985, pp. 477-481.
Sadoshima et al., "Inhibition of Angiotensin—Converting Enzyme Modulates the Autoregulation of Regional Cerebral Blood Flow in Hypertensive Rats," vol. 23, No. 6, Part 1, Jun. 1994, pp. 781-785.
Strandgaard et al., "Upper Limit of Cerebral Blood Flow Autoregulation in Experimental Renovascular Hypertension in the Baboon," vol. 37, Aug. 1975, pp. 164-167.
Ragauskas et al., "Analysis of cerebrovascular autoregulation reactivity index electronic monitoring methods," vol. 114, No. 8, Jun. 2011, 6 pp.
Chiu et al., "Assessment of cerebral autoregulation using time-domain cross-correlation analysis," Computers Bio Med, Nov. 2001, pp. 471-480.
Larson et al., "Cerebrovascular autoregulation after rewarming from hypothermia in a neonatal swine model of asphyxic brain injury," J Appl Physiol. 115; pp. 1433-1442, Sep. 2013.
Petkus et al., "Novel Method and Device for Fully Non-Invasive Cerebrovascular Autoregulation Monitoring," Elektronika Ir Elektrotechnika, vol. 20, No. 8, pp. 24-29, Oct. 2014.
Olufsen et al., "Blood pressure and blood flow variation during postural change from sitting to standing: model development and validation," J Appl Physiol Oct. 2005, pp. 1523-1537.
Rangel-Castilla, MD, et al., "Cerebral pressure autoregulation in traumatic brain injury," Neurosurg Focus, vol. 25, Oct. 2008, 8 pp.
Addison, "A Review of Wavelet Transform Time-Frequency Methods for NIRS-Based Analysis of Cerebral Autoregulation," IEEE Reviews in Biomedical Engineering, vol. 8, 2015, pp. 78-85.
Moerman, M.D., Ph.D., et al., "Assessment of Cerebral Autoregulation Patterns with Near-infrared Spectroscopy during Pharmacological-induced Pressure Changes," Anesthesiology, vol. 123, No. 2, Aug. 2015, pp. 327-335.
U.S. Appl. No. 15/911,449, naming Paul S. Addison et al. as inventors, filed Mar. 5, 2018.
U.S. Appl. No. 15/962,503, naming Paul S. Addison et al. as inventors, filed Apr. 25, 2018.
U.S. Appl. No. 15/980,235, naming Paul S. Addison et al. as inventors, filed May 15, 2018.
U.S. Appl. No. 15/962,468, naming Paul S. Addison et al. as inventors, filed Apr. 25, 2018.
U.S. Appl. No. 15/962,486, naming Dean Montgomery et al. as inventors, filed Apr. 25, 2018.

* cited by examiner

DETERMINING CHANGES TO AUTOREGULATION

TECHNICAL FIELD

This disclosure relates to monitoring the autoregulation of blood pressure.

BACKGROUND

Cerebral autoregulation (CA) is the response mechanism by which an organism regulates cerebral blood flow over a wide range of systemic blood pressure changes through complex myogenic, neurogenic, and metabolic mechanisms. Autoregulation dysfunction may result from a number of causes including, stroke, traumatic brain injury, brain lesions, brain asphyxia, or infections of the central nervous system. Intact cerebral autoregulation function occurs over a range of blood pressures defined between a lower limit of autoregulation (LLA) and an upper limit of autoregulation (ULA).

SUMMARY

This disclosure describes example regional oximetry devices configured to determine a limit of autoregulation based on a previously determined estimate of the limit of autoregulation and a newly determined estimate of the limit of autoregulation, referred to herein as a previous value of the limit of autoregulation and a first estimate of the limit of autoregulation, respectively. The regional oximetry device may be configured to determine a weighted average of the previously determined estimate and the newly determined estimate, where a weighting factor for the newly determined estimate is based on the difference between the newly determined estimate and other estimates of the limit of autoregulation. The regional oximetry device may determine the other estimates of the limit of autoregulation based on signals such as blood-pressure signals, oxygen saturation signals, blood volume signals, and/or any other signals.

Clause 1: In some examples, a device comprises a display and processing circuitry configured to receive a first signal indicative of a first physiological parameter of a patient and a second signal indicative of a second physiological parameter of the patient. The processing circuitry is also configured to determine a first estimate of a limit of autoregulation of the patient based on the first signal and the second signal and determine a difference between the first estimate of the limit of autoregulation and one or more other estimates of the limit of autoregulation. The processing circuitry is further configured to determine a weighted average of the first estimate of the limit of autoregulation and a previous value of the limit of autoregulation based on the difference between the first estimate of the limit of autoregulation and the one or more other estimates of the limit of autoregulation. The processing circuitry is configured to output, for display via the display, an indication of the autoregulation status.

Clause 2: In some examples of clause 1, the processing circuitry is configured to determine the difference between the first estimate and the one or more other estimates by at least determining a mean of the first estimate of the limit of autoregulation and the one or more other estimates of the limit of autoregulation, determining a mean absolute difference between the first estimate of the limit of autoregulation and a mean of the one or more other estimates of the limit of autoregulation, and determining a normalized difference by at least dividing the mean absolute difference by the mean of the first estimate and the one or more other estimates.

Clause 3: In some examples of clause 2, the processing circuitry is further configured to determine a multiplier by at least subtracting the normalized difference from one. The processing circuitry is configured to determine the weighted average by at least determining a weighting factor for the first estimate of the limit of autoregulation by multiplying a predetermined maximum weighting factor by the multiplier.

Clause 4: In some examples of clause 3, the processing circuitry is further configured to determine a new value of the limit of autoregulation based on the weighted average and output, for display via the display, an indication of the new value of the limit of autoregulation.

Clause 5: In some examples of any of clauses 1-4, the processing circuitry is configured to determine the difference between the first estimate and the one or more other estimates by at least determining a standard deviation of the first estimate of the limit of autoregulation and the one or more other estimates of the limit of autoregulation. The processing circuitry is further configured to determine a weighting factor based on the standard deviation of the first estimate and the one or more other estimates. The processing circuitry is configured to determine the weighted average of the first estimate of the limit of autoregulation and a previous value of the limit of autoregulation based on the weighting factor.

Clause 6: In some examples of any of clauses 1-5, the processing circuitry is configured to determine the difference between the first estimate and the one or more other estimates by at least determining a mean of the one or more other estimates of the limit of autoregulation, determining a mean absolute difference between the first estimate of the limit of autoregulation and the mean of the one or more other estimates, and determining a normalized difference by at least dividing the mean absolute difference by the mean of the first estimate and the one or more other estimates.

Clause 7: In some examples of any of clauses 1-6, the processing circuitry is configured to determine the weighted average by at least determining a first weighting factor and a second weighting factor based on the difference between the first estimate of the limit of autoregulation and the one or more other estimates of the limit of autoregulation, determining a first weighted value of the first estimate of the limit of autoregulation based on the first weighting factor, determining a second weighted value of the previous value of the limit of autoregulation based on the second weighting factor, and determining a sum of the first weighted value and the second weighted value.

Clause 8: In some examples of clause 7, determining the first weighted value comprises multiplying the first weighting factor and the first estimate of the limit of autoregulation. Determining the second weighting factor comprises subtracting the first weighting factor from one. Determining the second weighted value comprises multiplying the second weighting factor and the previous value of the limit of autoregulation.

Clause 9: In some examples of any of clauses 1-8, the second physiological parameter comprises a blood pressure of the patient, and the processing circuitry is further configured to determine a mean arterial pressure of the patient based on the second signal. The processing circuitry is configured to determine the autoregulation status by at least determining whether the mean arterial pressure is greater than or equal to the weighted average.

Clause 10: In some examples of clause 9, the processing circuitry is further configured to determine that the mean arterial pressure is less than or equal to the weighted average for more than a predetermined period of time, generate a notification in response to determining that the mean arterial pressure is less than or equal to the weighted average for more than the predetermined period of time, and output the notification.

Clause 11: In some examples of any of clauses 1-10, the first physiological parameter comprises an oxygen saturation of the patient, the second physiological parameter comprises a blood pressure of the patient, and the sensing circuitry is further configured to receive a third signal indicative of a blood volume of the patient. The processing circuitry is configured to determine the one or more other estimates of the limit of autoregulation by at least determining a second estimate of the limit of autoregulation based on first signal, determining a third estimate of the limit of autoregulation based on second signal and the third signal, and determining a fourth estimate of the limit of autoregulation based on the third signal.

Clause 12: In some examples of clause 11, the processing circuitry is configured to determine the second estimate by at least determining a set of oxygen saturation values of the patient based on the first signal. The processing circuitry is configured to determine the third estimate by at least determining a set of hemoglobin volume values of the patient based on the second signal and the third signal. The processing circuitry is configured to determine the fourth estimate by at least determining a set of blood volume values of the patient based on the third signal.

Clause 13: In some examples of any of clauses 1-12, wherein the processing circuitry is configured to determine the first estimate by at least determining a set of oxygen saturation values based on the first signal, determining a set of mean arterial pressure values based on the second signal, determining a set of correlation coefficients based on the set of oxygen saturation values and the set of mean arterial pressure values, and determining the first estimate based on the set of correlation coefficients.

Clause 14: In some examples of any of clauses 1-13, the processing circuitry is configured to determine the first estimate by at least determining a set of blood volume values based on the first signal, determining a set of mean arterial pressure values based on the second signal, determining a set of correlation coefficients based on the set of blood volume values and the set of mean arterial pressure values, and determining the first estimate based on the set of correlation coefficients.

Clause 15: In some examples of any of clauses 1-14, the processing circuitry is further configured to receive updated data for the first signal, receive updated data for the second signal, and set the previous value of the limit of autoregulation equal to the weighted average. The processing circuitry is also configured to determine an updated first estimate of the limit of autoregulation of the patient based on the updated data for the first signal and the updated data for the second signal. The processing circuitry is configured to determine an updated difference between the updated first estimate and one or more other updated estimates of the limit of autoregulation. The processing circuitry is further configured to determine an updated weighted average of the updated first estimate and the previous value based on the updated difference, determine an updated autoregulation status based on the updated weighted average, and output, for display via the display, an indication of the updated autoregulation status.

Clause 16: In some examples of any of clauses 1-15, the device further comprises sensing circuitry configured to generate the first and second signals.

Clause 17: In some examples of any of clauses 1-16, the processing circuitry is further configured to determine that a rate of change of the weighted average exceeds a threshold rate for at least a threshold time duration. The processing circuitry is also configured to cease determining the autoregulation status in response to determining that the rate of change of the weighted average exceeds the threshold rate for at least the threshold time duration.

Clause 18: In some examples, a method comprises receiving, by processing circuitry and from sensing circuitry, a first signal indicative of a first physiological parameter of a patient and a second signal indicative of a second physiological parameter of the patient. The method also comprises determining, by the processing circuitry, a first estimate of a limit of autoregulation of the patient based on the first signal and the second signal and a difference between the first estimate of the limit of autoregulation and one or more other estimates of the limit of autoregulation. The method further comprises determining, by the processing circuitry, a weighted average of the first estimate of the limit of autoregulation and a previous value of the limit of autoregulation based on the difference between the first estimate of the limit of autoregulation and the one or more other estimates of the limit of autoregulation. The method comprises determining, by the processing circuitry, an autoregulation status based on the weighted average and outputting, by the processing circuitry for display via the display, an indication of the autoregulation status.

Clause 19: In some examples, a device comprises a display and processing circuitry configured to receive a first signal indicative of a first physiological parameter of a patient, a second signal indicative of a second physiological parameter of the patient, and a third signal indicative of a third physiological parameter of the patient. The processing circuitry is also configured to determine a first estimate of a limit of autoregulation of the patient and two or more estimates of the limit of autoregulation based on the first signal, the second signal, and the third signal. The processing circuitry is configured to determine a difference between the first estimate of the limit of autoregulation and two or more other estimates of the limit of autoregulation. The processing circuitry is further configured to determine a weighting factor based on the difference between the first estimate and the two or more other estimates and determine a weighted average of the first estimate of the limit of autoregulation and a previous value of the limit of autoregulation based on the weighting factor. The processing circuitry is configured to determine an autoregulation status based on the weighted average.

Clause 20: In some examples of clause 19, the processing circuitry is configured to determine the difference between the first estimate and the two or more other estimates by at least determining a mean of the first estimate of the limit of autoregulation and the two or more other estimates of the limit of autoregulation, determining a mean absolute difference between the first estimate of the limit of autoregulation and a mean of the two or more other estimates of the limit of autoregulation, and determining a normalized difference by at least dividing the mean absolute difference by the mean of the first estimate and the two or more other estimates. The processing circuitry is further configured to determine a multiplier based on the normalized difference. The processing circuitry is configured to determine the weighted average by at least determining a weighting factor for the first estimate of the limit of autoregulation by multiplying a predetermined maximum weighting factor by the multiplier.

Clause 21: In some examples, a device comprises sensing circuitry configured to receive a first signal indicative of a first physiological parameter of a patient and a second signal indicative of a second physiological parameter of the patient. The device also comprises processing circuitry configured to determine a first estimate of a limit of autoregulation of the patient based on the first signal and the second signal and determine a difference between the first estimate of the limit of autoregulation and one or more other estimates of the limit of autoregulation. The processing circuitry is further configured to determine a weighted average of the first estimate of the limit of autoregulation and a previous value of the limit of autoregulation based on the difference between the first estimate of the limit of autoregulation and the one or more other estimates of the limit of autoregulation.

The details of one or more examples are set forth in the accompanying drawings and the description below. Other features, objects, and advantages will be apparent from the description and drawings, and from the claims.

DETAILED DESCRIPTION

Figure 1:
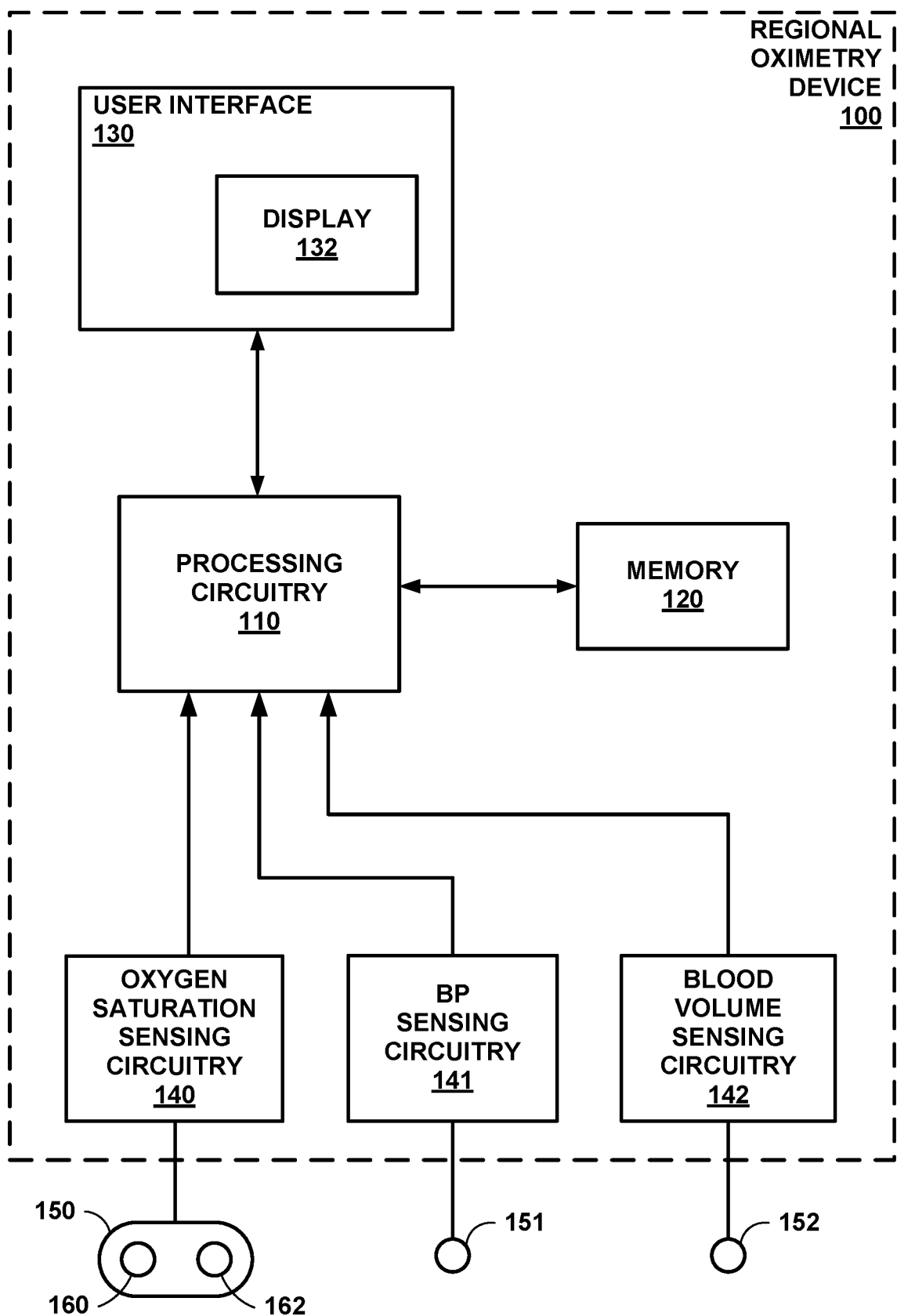
FIG. 1 is a conceptual block diagram illustrating an example regional oximetry device.

This disclosure describes devices, systems, and techniques for determining changes in cerebral autoregulation of a patient. A system may include a regional oximetry device that includes processing circuitry configured to determine the cerebral autoregulation status of the patient based on a limit of autoregulation, also referred to as a limit of cerebral autoregulation, such as the lower limit of autoregulation (LLA) and/or the upper limit of autoregulation (ULA). In order to determine the LLA and/or the ULA, the processing circuitry is configured to determine a weighted average of a previous value of the limit of autoregulation and a first estimate of the limit of autoregulation. The processing circuitry can then determine the cerebral autoregulation status of the patient by comparing the blood pressure of the patient to the weighted average in order to determine whether the blood pressure indicates that the patient has intact or impaired cerebral autoregulation.

The processing circuitry may be configured to use the most recent iteration of the weighted average as the previous value of the limit of autoregulation for the next iteration of the weighted average. The processing circuitry may also be configured to determine the first estimate of the limit of autoregulation based on two physiological signals received from the patient. The two physiological signals can be signals that indicate blood pressure and oxygen saturation, for example. In some examples, the processing circuitry determines the first estimate of the limit of autoregulation based on a correlation index (COx) of the blood pressure and oxygen saturation.

The processing circuitry may continually update the weighted average as part of determining the cerebral autoregulation status of the patient. The devices, systems, and techniques described herein may increase the accuracy of the determination of the cerebral autoregulation status of a patient by removing, dampening, or reducing the weighting of outlier estimates from the algorithm used to determine a limit of cerebral autoregulation. For example, if an estimate of a limit of autoregulation based on COx values is relatively far removed from other estimates of the limit of autoregulation, then the processing circuitry can reduce the weighting of the far-removed estimate of the limit of autoregulation.

A patient state, as indicated by sensed physiological signals, may change relatively rapidly over time. In response to a changing patient state, some estimates of a limit of autoregulation may change quickly, while other estimates may change more slowly. In some examples, the slowly changing estimate will be inaccurate during a time interval after the change in patient state. Other possible causes of large differences between estimates of limits of cerebral autoregulation include electrocautery, damping of blood pressures due to catherization of the patient, changes in sensed blood pressure due to probe (e.g., sensor) movement relative to the patient, and changes in sensed blood pressure due to line flushing. Processing circuitry that reduces the weighting of outlier estimates may determine a weighted average that is more accurate, as compared to processing circuitry that does not reduce the weighting of outlier estimates.

The processing circuitry may determine a first estimate of a limit of autoregulation based on a specific parameter or correlation coefficient. This disclosure primarily describes processing circuitry configured to determine a first estimate based on COx values, but, alternatively or additionally, the processing circuitry may be configured to determine a first estimate based on other parameters or correlation coefficients. When the processing circuitry determines a current first estimate of the limit of autoregulation, the processing circuitry does not necessarily discard the previous estimate of the limit of autoregulation. Instead, the processing circuitry determines a weighted average of the current first estimate and the previous estimate of the limit of autoregulation. In some examples, the processing circuitry weighs the previous estimate more heavily than the current first estimate.

In response to determining that the current first estimate is an outlier relative to other estimates, then the processing circuitry reduces the weight of the current first estimate, possibly to zero. If the current first estimate has zero weight, then the processing circuitry effectively reuses the previous estimate of the limit of autoregulation. Thus, in response to determining a relatively large difference between the current first estimate and other estimates (e.g., based on other parameters), the processing circuitry may be configured to determine a small weighting factor for the current first estimate and a large weighting factor for the previous estimate. Reducing the weighting factor for the current first estimate based on the difference between the current first estimate and the other estimates may increase the accuracy and the stability of the determination of the limit of autoregulation. The reduced weighting factor may increase stability because the processing circuitry can filter out or dilute inaccurate estimates by reducing the weight of the inaccurate estimates in the determination of the weighted average.

The devices, systems, and techniques of this disclosure may increase the accuracy of the presentation of an estimate of a limit of autoregulation of a patient and the presentation of an indication of the autoregulation status of the patient. The presentation of more accurate and more stable information may result in increased confidence by a clinician viewing the presented information, which may lead to more informed decision making by the clinician. A clinician may lose confidence in the information presented by the processing circuitry if the information is unstable and/or inaccurate.

To quickly ascertain the cerebral autoregulation status, a clinician may seek a single robust value of a limit of autoregulation based on a known parameter, such as COx or HVx. The devices, systems, and techniques of this disclosure may provide a single determination of the autoregulation status of a patient, rather than multiple parameters with multiple estimates of a limit of autoregulation that may be confusing or impractical to a clinician, e.g., view of some existing cerebral autoregulation monitoring devices. The devices, systems, and techniques of this disclosure can avoid combining multiple parameters in a way that may result in a combined parameter unfamiliar to the clinician.

The autoregulation status of a patient may be an indication that the cerebral autoregulation control mechanism of the patient is intact (e.g., functioning properly) or impaired. Cerebral blood flow (CBF) may be regulated over a range of systemic blood pressures by the cerebral autoregulation control mechanism. This range may lie within the LLA and ULA, beyond which blood pressure drives CBF, and cerebral autoregulation function may be considered impaired. One method to determine the limits of autoregulation (the LAs) noninvasively using near-infrared spectroscopy (NIRS) technology may be via the COx measure: a moving correlation index between mean arterial pressure (MAP) and regional oxygen saturation ($rSO_2$).

When the cerebral autoregulation is intact for a patient, there is typically no correlation between MAP and $rSO_2$. In contrast, MAP and $rSO_2$ typically directly correlate (e.g., the correlation index of COx is approximately 1) when the cerebral autoregulation is impaired. In practice, however, sensed data indicative of autoregulation may be noisy and/or there might be a slightly correlated relationship between variables (e.g., MAP and $rSO_2$) even when cerebral autoregulation is intact for the patient.

Some existing systems for monitoring autoregulation may determine a patient's autoregulation status based on various physiological parameter values (also referred to herein as physiological values). Such physiological values may be subject to various sources of error, such as noise caused by relative sensor and patient motion, operator error, poor quality measurements, drugs, or other anomalies. However, some existing systems for monitoring autoregulation may not reduce the various sources of error when utilizing the measured physiological values to determine the patient's autoregulation status. Furthermore, some existing systems may not determine and/or utilize a reliable metric to determine whether the autoregulation status calculated from the physiological values is reliable. Accordingly, the autoregulation status determined by such existing systems may be less accurate or less reliable.

In some examples, a regional oximetry device of this disclosure may include processing circuitry configured to determine estimates of a limit of cerebral autoregulation based on a patient's MAP and a patient's oxygen saturation. In particular, the processing circuitry may determine estimates of a limit of cerebral autoregulation based on oxygen saturation ($LArSO_2$) and based on a set of COx values (LACOx). In addition, the processing circuitry may monitor the patient's autoregulation by correlating measurements of the patient's blood pressure with measurements of the patient's blood volume (BVS) and by determining an estimate of the limit of cerebral autoregulation based on the BVS values (LABVS). The processing circuitry can determine a hemoglobin volume index (HVx) based at least in part on a linear correlation between the patient's blood pressure and blood volume. The processing circuitry can then determine an estimate of the limit of cerebral autoregulation based on the HVx values (LAHVx). The processing circuitry may also determine various other linear correlations to help evaluate a patient's autoregulation status, such as a linear correlation between measurements of a patient's blood pressure and measurements of a patient's cerebral blood flow known as a mean velocity index (Mx). The processing circuitry may also determine a linear correlation between measurements of a patient's blood pressure and measurements of a patient's intracranial pressure known as a pressure reactivity index (PRx). Mx may be a proxy for COx, and PRx may be a proxy for HVx.

Additional example details of the parameters that can be used for determining a limit of autoregulation may be found in commonly assigned U.S. Patent Application Publication No. 2017/0105631 filed on Oct. 18, 2016, entitled "Systems and Method for Providing Blood Pressure Safe Zone Indication During Autoregulation Monitoring," commonly assigned U.S. patent application Ser. No. 15/184,305 filed on Jun. 6, 2016, entitled "Systems and Methods for Reducing Signal Noise When Monitoring Autoregulation," and commonly assigned U.S. patent application Ser. No. 15/296, 150 filed on Oct. 18, 2016, entitled "System and Method for Providing Blood Pressure Safe Zone Indication During Autoregulation Monitoring," which are incorporated herein by reference in their entirety.

FIG. 1 is a conceptual block diagram illustrating an example regional oximetry device 100. Regional oximetry device 100 includes processing circuitry 110, memory 120, user interface 130, display 132, sensing circuitry 140-142, and sensing device(s) 150-152. In some examples, regional oximetry device 100 may be configured to determine and display the cerebral autoregulation status of a patient, e.g., during a medical procedure or for more long-term monitoring, such as fetal monitoring. A clinician may receive information regarding the cerebral autoregulation status of a patient via display 132 and adjust treatment or therapy to the patient based on the cerebral autoregulation status information.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of physiological parameters, MAP values, $rSO_2$ values, COx values, BVS values, HVx values, and value(s) of an LLA and/or a ULA, for example. Memory 120 may also be configured to store data such as weighting factors, maximum weighting factors, threshold values, and/or threshold levels, which may be predetermined by processing circuitry 110. The weighting factors, maximum weighting factors, threshold values, and/or threshold levels may stay constant throughout the use of device 100 and across multiple patients, or these values may change over time.

In some examples, memory 120 may store program instructions, which may include one or more program modules, which are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a subject. For example, processing circuitry 110 may be configured to present blood pressure values, physiological parameter values, and indications of autoregulation status (e.g., cerebral autoregulation status) of a patient via display 132. In some examples, if processing circuitry 110 determines that the autoregulation status of the patient is impaired, then processing circuitry 110 may present a notification (e.g., an alert) indicating the impaired cerebral autoregulation status via display 132. As another example, processing circuitry 110 may present, via display 132, estimates of $rSO_2$ for a patient, an estimate of the blood oxygen saturation ($SpO_2$) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, a light emitting diode (LED) display, and/or any other suitable display. User interface 130 and/or display 132 may be part of a personal digital assistant, mobile phone, tablet computer, laptop computer, any other suitable computing device, or any combination thereof, with a built-in display or a separate display. User interface 130 may also include means for projecting audio to a user, such as speaker(s). Processing circuitry 110 may be configured to present, via user interface 130, a visual, audible, tactile, or somatosensory notification (e.g., an alarm signal) indicative of the patient's autoregulation status. User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., communication interface 290 shown in FIG. 2).

Sensing circuitry 140-142 may be configured to receive physiological signals sensed by respective sensing device(s) 150-152 and communicate the physiological signals to processing circuitry 110. Sensing device(s) 150-152 may include any sensing hardware configured to sense a physiological parameter of a patient, such as, but not limited to, one or more electrodes, optical receivers, blood pressure cuffs, or the like. Sensing circuitry 140-142 may convert the physiological signals to usable signals for processing circuitry 110, such that processing circuitry 110 is configured to receive signals generated by sensing circuitry 140-142. Sensing circuitry 140-142 may receive signals indicating physiological parameters from a patient, such as, but not limited to, blood pressure, regional oxygen saturation, blood volume, heart rate, and respiration. Sensing circuitry 140-142 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140-142 and/or processing circuitry 110 may include signal processing circuitry such as an analog-to-digital converter.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the range of about 600 nanometers (nm) to about 1000 nm. In a particular example, one LED of emitter 160 is configured to emit light at about 730 nm and the other LED of emitter 160 is configured to emit light at about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160. Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

In operation, blood pressure sensing device 151 and oxygen saturation sensing device 150 may each be placed on the same or different parts of the patient's body. For example, blood pressure sensing device 151 and oxygen saturation sensing device 150 may be physically separate from each other and may be separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). For example, blood pressure sensing device 151 may include a blood pressure cuff for non-invasively monitoring blood pressure or an arterial line for invasively monitoring blood pressure. In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 151 may be configured to generate a blood pressure signal indicative of the patient's blood pressure (e.g., arterial blood pressure) over time. Blood pressure sensing device 151 may provide the blood pressure signal to sensing circuitry 141, processing circuitry 110, or to any other suitable processing device to enable evaluation of the patient's autoregulation status.

Processing circuitry 110 may be configured to receive one or more signals generated by sensing devices 150-152 and sensing circuitry 140-142. The physiological signals may include a signal indicating blood pressure, a signal indicating oxygen saturation, and/or a signal indicating blood volume of a patient (e.g., an isosbestic signal). Processing circuitry 110 may be configured to determine a first estimate of a limit of autoregulation based on two or more signals received by sensing devices 150-152 and sensing circuitry 140-142 and delivered to processing circuitry 110. Sensing devices 150-152 and sensing circuitry 140-142 can deliver the physiological signals directly to processing circuitry 110 or sensing circuitry 140-142 can modify the physiological signals (e.g., through pre-processing) before delivering signals to processing circuitry 110.

In some examples, processing circuitry 110 determines the first estimate of the limit of autoregulation based on a correlation index (e.g., COx, HVx), an oxygen saturation value, a blood volume value, a gradients measure, and/or another physiological parameter of the first and second physiological signals. Although described herein primarily as LACOx, the first estimate may also be based on other physiological parameters or physiological indices, such as LAHVx, LArSO2, LABVS, or an estimate of the limit of autoregulation based on Mx or PRx. For example, Equations (1)-(5) below use $LACOx_{current}$ as the first estimate of the limit of autoregulation, but processing circuitry 110 can use other physiological parameters to determine the first estimate.

Processing circuitry 110 may use any of several techniques to determine the first estimate of the limit of autoregulation. In some examples, processing circuitry 110 determines a set of COx values based on MAP values and $rSO_2$ values. Processing circuitry 110 may then determine an estimate of a lower limit of autoregulation based on the lowest blood pressure value at which the expected value of COx is less than a threshold value, such as 0.5, 0.4, 0.3, 0.2, 0.1, or 0.0. Using this threshold value, processing circuitry 110 can determine where there is a distinct change in the gradient of a $rSO_2$-MAP curve or a BVS-MAP curve. This distinct change may correspond to a distinct step down in the plot of COx or HVx versus MAP. Similarly, processing circuitry 110 may determine an estimate of an upper limit of autoregulation based on the highest blood pressure value at which the expected value of COx is less than a threshold value. Additional example details of determining LAs and cerebral autoregulation status may be found in commonly assigned U.S. Patent Application Publication No. 2018/0014791, filed on Jul. 13, 2017, the entire content of which is incorporated herein by reference.

Processing circuitry 110 is also configured to determine one or more other estimates of the limit of autoregulation, such as $LArSO_2$, LABVS, LAHVx, and/or any other estimate of the limit of autoregulation. For example, $LArSO_2$, LAHVx, and LABVS in Equations (1), (5), (6), and (11) below represent the other estimates of the limit of autoregulation, although processing circuitry 110 may determine different, greater than, or fewer than three other estimates of the limit of autoregulation in some examples. Processing circuitry 110 may determine the other estimates of the limit of autoregulation using example thresholds and/or other methods described with respect to FIGS. 4A-4D. Additional example details of determining estimates of LAs may be found in commonly assigned U.S. Patent Application Publication No. 2018/0049649 filed on Aug. 1, 2017, and entitled "System and Method for Identifying Blood Pressure Zones During Autoregulation Monitoring," and in commonly assigned U.S. Patent Application Publication No. 2016/0367197 filed on Dec. 22, 2016, and entitled "Systems and Methods of Reducing Signal Noise when Monitoring Autoregulation," the entire contents of each of which are incorporated herein by reference.

Processing circuitry 110 may be configured to determine a difference between the first estimate of the limit of autoregulation and the one or more other estimates of the limit of autoregulation. The difference may indicate whether the first estimate of the limit of autoregulation is an outlier estimate of the limit of autoregulation relative to the other estimates, or whether the first estimate of the limit of autoregulation is closely aligned with the other estimates. One possible reason for the first estimate of the limit of autoregulation being an outlier estimate is that the first estimate of the limit of autoregulation is an inaccurate estimate. Another possible reason for the first estimate of the limit of autoregulation being an outlier estimate is that some or all of the other estimates are inaccurate estimates.

Equation (1) shows one example technique for determining a mean absolute difference (MADCOx) between the first estimate of the limit of autoregulation and the other estimates (LArSO$_2$, LAHVx, and LABVS). In Equation (1), the mean absolute difference equals the absolute value of the difference between the first estimate of the limit of autoregulation and the mean of three other estimates.

$$\text{MADCOx} = |\text{LACOx}_{current} - \tfrac{1}{3}(\text{LArSO}_2 + \text{LAHVx} + \text{LABVS})| \qquad (1)$$

The MADCOx value may serve as a quality metric for the currently computed LACOx value, such that a relatively large MADCOx can indicate a higher possibility of inaccuracies. Processing circuitry 110 may be configured to use this quality metric to weight the currently calculated LLACOx value when processing circuitry 110 adds the current estimate to the current reported value (e.g., the previous estimate) on display 132 to provide an updated reported value (see, e.g., Equation (2)). Processing circuitry 110 may use the other estimates to give or remove confidence from the first estimate. Processing circuitry 110 may look at the other estimates to determine whether the first estimate is an outlier estimate. If processing circuitry 110 determines that the first estimate is an outlier estimate, processing circuitry 110 may be configured to reduce the weighting of the first estimate in the determination of a weighted average.

Processing circuitry 110 is configured to then determine a weighted average of the first estimate of the limit of autoregulation and a previous value of the limit of autoregulation. To determine the weighted average, processing circuitry 110 can use the difference between the first estimate of the limit of autoregulation and the other estimates to determine a weighting factor for the first estimate of the limit of autoregulation. In some examples, processing circuitry 110 can reduce a magnitude of the weighting factor of the first estimate of the limit of autoregulation based on determining a relatively large difference between the first estimate of the limit of autoregulation and the other estimates. The relatively large difference may indicate that the first estimate of the limit of autoregulation is inaccurate. Thus, by reducing the weighting factor of the first estimate of the limit of autoregulation, processing circuitry 110 may insulate the weighted average, and consequently the determination of an autoregulation status of a patient, from a possibly inaccurate first estimate of the limit of autoregulation. Conversely, processing circuitry 110 may increase the weighting factor based on a relatively small difference between the first estimate of the limit of autoregulation and the other estimates.

Equations (2)-(9) show example techniques by which processing circuitry 110 may determine a weighted average of the first estimate of the limit of autoregulation and a previous value of the limit of autoregulation. As shown in Equation (2), processing circuitry 110 can determine a weighted average (LACOx$_{new}$) based on a previous value of the limit of autoregulation (LACOx$_{previous}$), which may be the most recently determined weighted average. Thus, if the newly determined weighted average is the Nth iteration of the weighted average, then processing circuitry 110 may set the previous value of the limit of autoregulation equal to the (N−1)th iteration of the weighted average. Processing circuitry 110 may multiply the first estimate of the limit of autoregulation (LACOx$_{current}$) by a first weighting factor (w) that is between zero and one. Processing circuitry 110 may also multiply the previous value of the limit of autoregulation by a second weighting factor that is equal to the one minus the first weighting factor. Thus, in the example of Equation (2), the sum of the two weighting factors is one. Processing circuitry 110 can use Equations (3) and (4) to determine the weighted values that make up the weighted average.

$$\text{LACOx}_{new} = [(1-w) \times \text{LACOx}_{previous}](w \times \text{LACOx}_{current}) \qquad (2)$$

$$\text{Weighted value of first estimate} = w \times \text{LACOx}_{current} \qquad (3)$$

$$\text{Weighted value of previous value} = (1-w) \times \text{LACOx}_{previous} \qquad (4)$$

In Equation (2), LACOx$_{new}$ may represent the new reported value, e.g., on a device screen. For example, processing circuitry 110 can output, to display 132, LACOx$_{new}$ for presentation to a user. LACOx$_{previous}$ may represent the previously reported value by processing circuitry 110 on the device screen (e.g., display 132). LACOx$_{current}$ may represent the first estimate of the limit of autoregulation based on currently calculated COx values by processing circuitry 110 of device 100 using the latest acquired signal portions from sensing devices 150-152. Processing circuitry 110 may not necessarily output LACOx$_{current}$ for display, because in some examples processing circuitry 110 may use LACOx$_{current}$ only to determine LACOx$_{new}$.

Processing circuitry 110 can determine the first weighting factor using the example techniques of Equations (5)-(9), although other techniques may be used in other examples. In some examples, processing circuitry 110 may determine a normalized difference (MADCOx divided by $\mu_{LA}$) based on the difference between the first estimate of the limit of autoregulation and the other estimates. Processing circuitry 110 may be configured to normalize the difference by dividing the difference by the mean ($\mu_{LA}$) of the first estimate of the limit of autoregulation and the other estimates. Processing circuitry 110 may determine the mean of the estimates $\mu_{LA}$ as shown in Equation (5). By normalizing the difference using Equation (7), processing circuitry 110 may determine a percentage difference rather than a difference in absolute terms. In some examples, processing circuitry 110 may determine the mean based on only the other estimates by excluding or leaving out the first estimate, as shown in Equation (6).

$$\mu_{LA} = \tfrac{1}{4}(LACOx_{current} + LArSO_2 + LAHVx + LABVS) \qquad (5)$$

-continued $$\mu_{LA} = \frac{1}{3}(LArSO_2 + LAHVx + LABVS) \quad (6)$$

$$\text{Normalized difference} = \frac{MADCOx}{\mu_{LA}} \quad (7)$$

$$m = 1 - \frac{MADCOx}{\mu_{LA}} \quad (8)$$

$$w = w_s \times m = w_s - \frac{w_s \times MADCOx}{\mu_{LA}} \quad (9)$$

Processing circuitry 110 can then use the normalized difference to determine the first weighting factor (w) by multiplying a predetermined maximum weighting factor ($w_s$) by one minus the normalized difference, as shown in Equations (7)-(9). Processing circuitry 110 may determine the first weighting factor based on the similarity between the COx value of the limit of autoregulation and estimates from the other method. The magnitude of the weighting factor effectively represents a trade-off between the amount of trust given to previous values of the limit of autoregulation versus the current value of the limit of autoregulation weighted average. In some examples, the predetermined maximum weighting factor may be set or determined based on empirical data.

Processing circuitry 110 may store the predetermined maximum weighting factor to memory 120 as a value between zero and one, such as 0.1, 0.2, 0.3, 0.4, or any other suitable value. The weighting factor may be scaled version of the predetermined maximum weighting factor, where a maximum value of the weighting factor is the value of the predetermined maximum weighting factor. Processing circuitry 110 may also store an initial weighting factor value to memory 120 for use before processing circuitry 110 has determined a multiplier.

Thus, in response to determining a relatively large difference using Equation (1), processing circuitry 110 may determine a relatively small multiplier (e.g., an "m" factor) using Equation (8) and a relatively small first weighting factor using Equation (9). In some examples, the multiplier may be a simple metric multiplier equal to unity (e.g., one) if all points agree and less than unity if the points differ from LACOx. Processing circuitry 110 may be configured to determine the multiplier by subtracting the normalized difference from one. If the value of the multiplier is less than zero, then processing circuitry 110 may set the value of the multiplier to zero. Processing circuitry 110 may then produce the weighting factor from a standard weight (e.g., a predetermined maximum weighting factor) and the multiplier using Equation (9). A small value of the first weighting factor may result in processing circuitry 110 determining a weighted average based on a heavily weighted previous value of the limit of autoregulation and a lightly weighted first estimate of the limit of autoregulation using Equation (2). In this manner, processing circuitry 110 may be configured to dampen or reduce the change in the weighted average from one iteration to the next iteration based on determining a relatively large difference between the first estimate of the limit of autoregulation and the other estimates because the relatively large difference may result from an inaccurate first estimate of the limit of autoregulation.

In some examples, processing circuitry 110 is configured to determine an autoregulation status based on the weighted average of the first estimate of the limit of autoregulation and a previous value of the limit of autoregulation. For example, processing circuitry 110 can determine that a patient has intact autoregulation in response to determining that the blood pressure of the patient is greater than a lower limit of autoregulation and less than an upper limit of autoregulation (e.g., the blood pressure is between the limits of autoregulation).

Once the autoregulation status has been determined, processing circuitry 110 outputs, such as for display via display 132 of user interface 130, an indication of the autoregulation status. Display 132 may present a graphical user interface such as graphical user interface 300 shown in FIG. 3. As described in further detail below, graphical user interface 300 includes an indicator of autoregulation status 350. The indication of autoregulation status may include text, colors, and/or audio presented to a user. Processing circuitry 110 may be further configured to present an indication of one or more limits of autoregulation (e.g., indicators 360 and 370).

Although other example techniques are possible, regional oximetry device 100 may be configured to determine the first estimate of the limit of autoregulation based on COx values derived from MAP values and $rSO_2$ values. For example, processing circuitry 110 may determine the first estimate of the limit of autoregulation based on HVx values, BVS values, and/or $rSO_2$ values in order to determine a robust value of any of the other parameters. Regional oximetry device 200 of FIG. 2 includes additional detail on how processing circuitry 110 can determine $rSO_2$ values based on a physiological signal received from sensing device 150.

Figure 2:
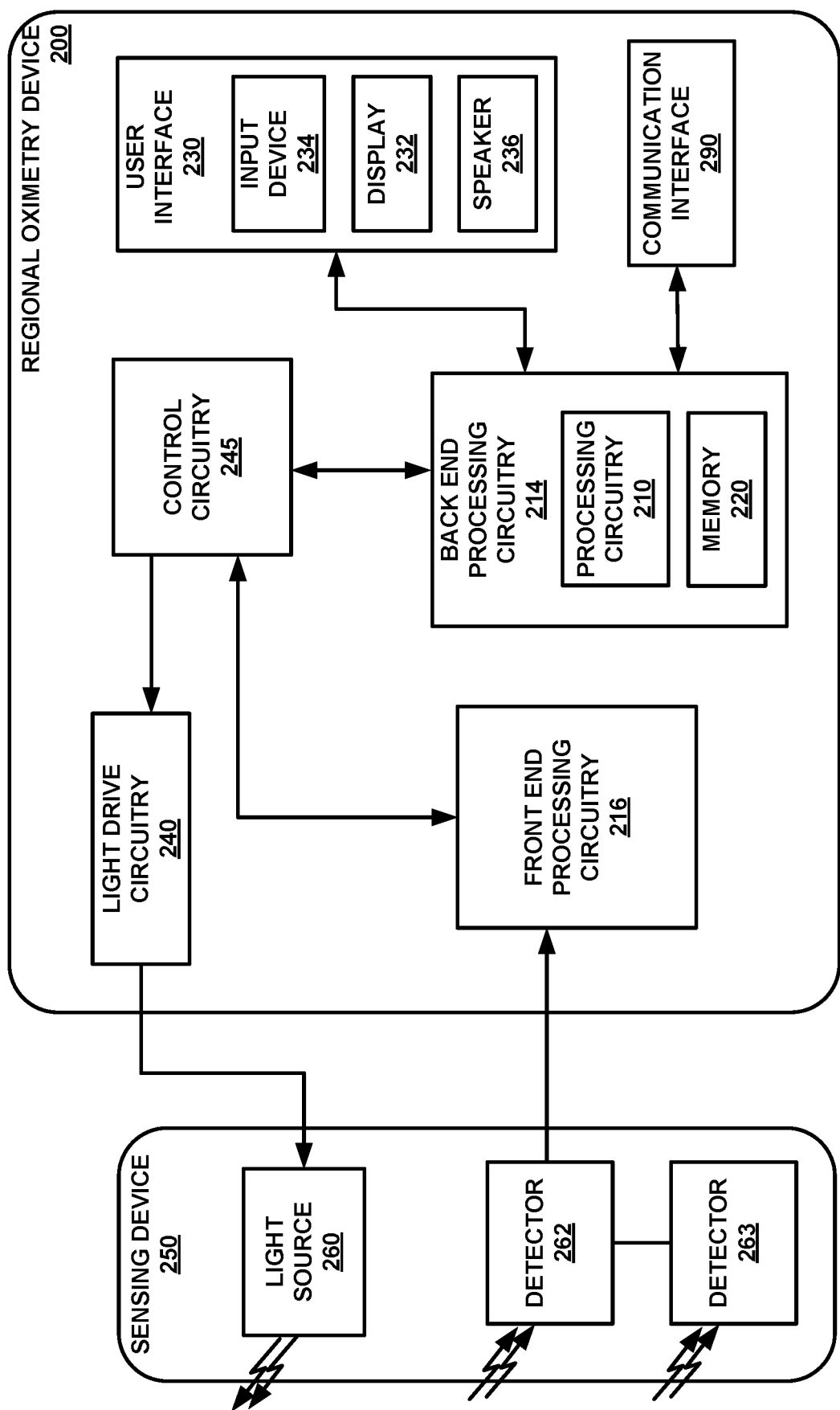
FIG. 2 is a conceptual block diagram illustrating an example regional oximetry device for monitoring the autoregulation status of a patient.

FIG. 2 is a conceptual block diagram illustrating an example regional oximetry device 200 for monitoring the autoregulation status of a patient. In the example shown in FIG. 2, regional oximetry device 200 includes sensing device 250 and regional oximetry device 200, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1 and regional oximetry device 200 shown in FIG. 2. In some examples, regional oximetry device 200 may also include a blood pressure sensor and/or a blood volume sensor (e.g., sensing devices 151 and 152).

In the example shown in FIG. 2, sensing device 250 includes light source 260, detector 262, and detector 263. In some examples, sending device 250 may include more than two detectors. Light source 260 may be configured to emit photonic signals having two or more wavelengths of light (e.g., red and infrared (IR)) into a subject's tissue. For example, light source 260 may include a red light emitting light source and an IR light emitting light source, (e.g., red and IR light emitting diodes (LEDs)), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, which may process the detection signals and determine physiological parameters (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters. Processing circuitry 210 is also configured to determine an autoregulation status based on a weighted average of a first estimate of a limit of autoregulation and a previous value of the limit of autoregulation. Processing circuitry 210 may be configured to determine a weighting factor for the determination of the weighted average based on a difference between the first estimate of the limit of autoregulation and one or more other estimates of the limit of autoregulation.

Memory 220 may include any suitable computer-readable media capable of storing information that can be interpreted by processing circuitry 210. In some examples, memory 220 may store reference absorption curves, reference sets, determined values, such as blood oxygen saturation, pulse rate, blood pressure, fiducial point locations or characteristics, initialization parameters, any other determined values, or any combination thereof, in a memory device for later retrieval. Memory 220 may also store a previously determined estimate of the limit of autoregulation, weighting factors, weighted values, and so on. Back-end processing circuitry 214 may be communicatively coupled with user interface 230 and communication interface 290.

User interface 230 may include input device 234, display 232, and speaker 236. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include any type of user input device such as a keyboard, a mouse, a touch screen, buttons, switches, a microphone, a joy stick, a touch pad, or any other suitable input device or combination of input devices. Input device 234 may also receive inputs to select a model number of sensing device 250, blood pressure sensor 250 (FIG. 2), or blood pressure processing equipment. In some examples, processing circuitry 210 may determine a predetermined maximum weighting factor based on user inputs received by input device 234.

Figure 3:
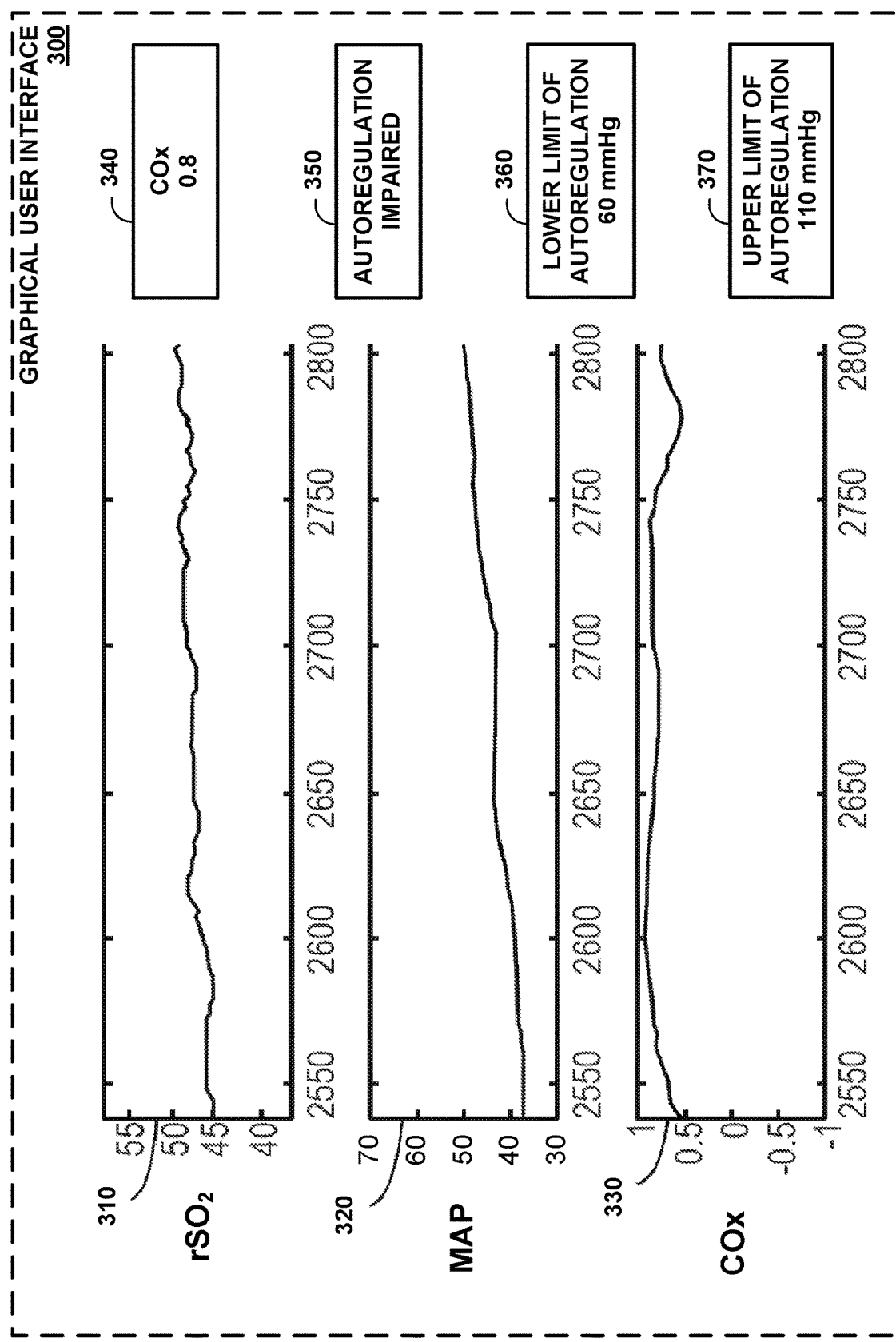
FIG. 3 illustrates an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2. Additionally, display 232 may present, for example, one or more estimates of a subject's regional oxygen saturation generated by regional oximetry device 200 (referred to as an "rSO2" measurement). Display 232 may also present indications of the upper and lower limits of autoregulation. Speaker 236 within user interface 230 may provide an audible sound that may be used in various examples, such as for example, sounding an audible alarm in the event that a patient's physiological parameters are not within a predefined normal range.

Communication interface 290 may enable regional oximetry device 200 to exchange information with external devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Graphical user interface 300 may be configured to display various information related to blood pressure, oxygen saturation, the COx index, limits of autoregulation, and/or autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value.

COx signal indicator 330 may present a set of correlation coefficients determined by processing circuitry 110. Processing circuitry 110 may determine the correlation coefficients as a function of the oxygen saturation values presented in oxygen saturation signal indicator 310 and the MAP values presented in blood pressure signal indicator 320. In some examples, a COx value at or near one indicates the autoregulation status of a patient is impaired, as shown in autoregulation status indicator 350.

COx value indicator 340 shows a COx value of 0.8, which may result in a determination by processing circuitry 110 that the autoregulation status of the patient is impaired. Processing circuitry 110 may be configured to present, as the COx value in COx value indicator 340, the most recently determined COx value. In order to determine the autoregulation status of a patient for presentation in autoregulation status indicator 350, processing circuitry 110 may determine whether the most recent MAP value shown in blood pressure signal indicator 320 is between the limits of autoregulation presented in limit of autoregulation indicators 360 and 370.

Processing circuitry 110 may present limit of autoregulation indicators 360 and/or 370 in terms of blood pressure, for example, millimeters of mercury (mmHg). Processing circuitry 110 may determine a weighted average of a first estimate and a previous value in order to determine a lower limit of autoregulation presented in indicator 360 or an upper limit of autoregulation presented in indicator 370. If processing circuitry 110 determines the lower limit of autoregulation based on a weighted average and determines that a MAP value is less than or equal to the weighted average, processing circuitry 110 may be configured to generate a notification in response to determining that the MAP value is less than or equal to the weighted average for more than a predetermined period of time. In response to determining that the MAP value is less than or equal to the weighted average for more than the predetermined period of time, processing circuitry 110 may output the notification in autoregulation status indicator 350 as text, color, blinking, and/or any other suitable visible or audible manner.

FIGS. 4A-4D are example graphs of $rSO_2$, COx, BVS, and HVx versus mean arterial pressure. Processing circuitry 110 is configured to determine one or more other estimates of the limit of autoregulation, such as $LArSO_2$, LABVS, LAHVx, and/or any other estimate of the limit of autoregulation. For example, $LArSO_2$, LAHVx, and LABVS in Equations (1), (5), and (6) above and Equation (11) below represent the other estimates of the limit of autoregulation, although processing circuitry 110 may determine different, more, or fewer than three other estimates of the limit of autoregulation in some examples.

Estimates 410A-410D represent four computed limits of autoregulation using respective methods. Each of estimates 410A-410D may not necessarily be equal to the other three of estimates 410A-410D. To determine an estimate of a limit of autoregulation, processing circuitry 110 may use different algorithms for each physiological parameter (e.g., $rSO_2$ and BVS) and for each correlation coefficient (e.g., COx and HVx). In some examples, processing circuitry 110 may be configured to determine four estimates of the limit of autoregulation based on the values of the two physiological parameters and the values of the two correlation coefficients. Although FIGS. 4A-5 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 4A-5.

Figure 4A:
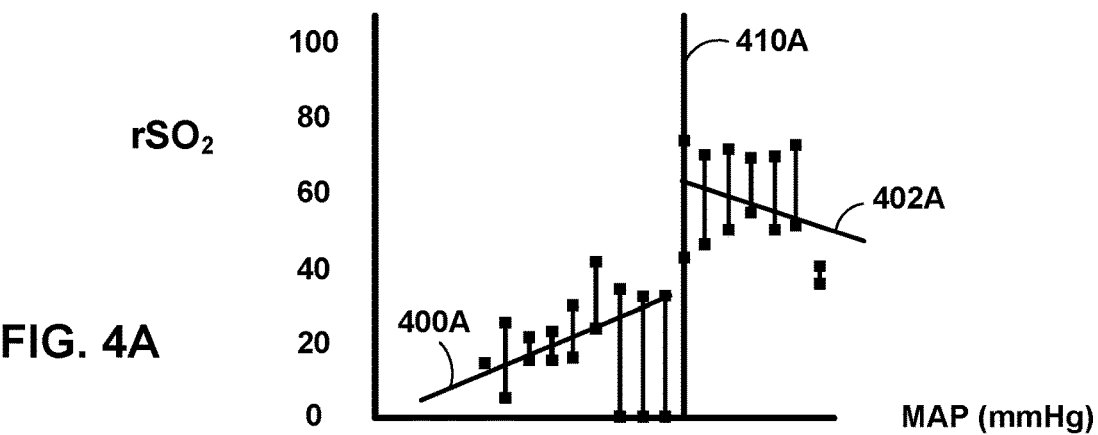
FIGS. 4A-4D are example graphs of oxygen saturation ($rSO_2$), correlation coefficient (COx), blood volume under sensor (BVS), and hemoglobin volume index (HVx) versus mean arterial pressure.
Figure 4B:
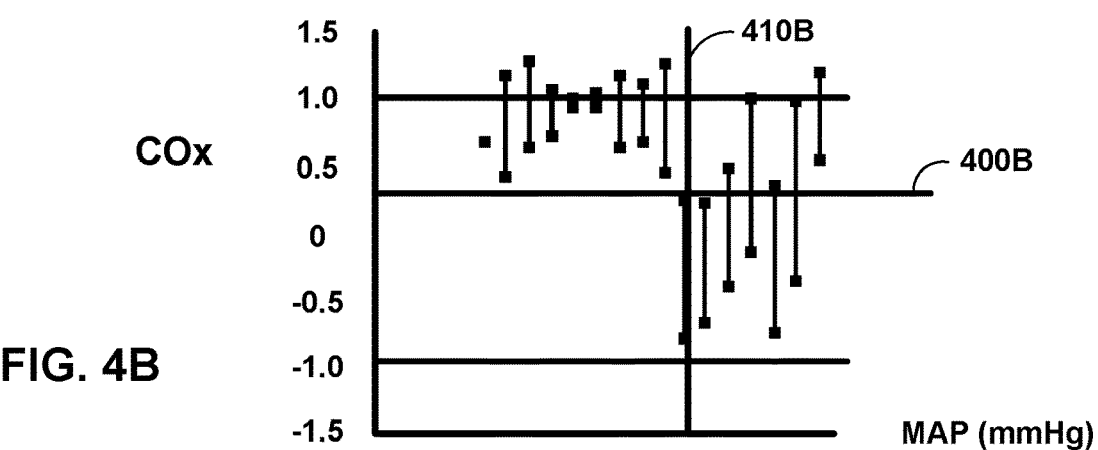
Figure 4C:
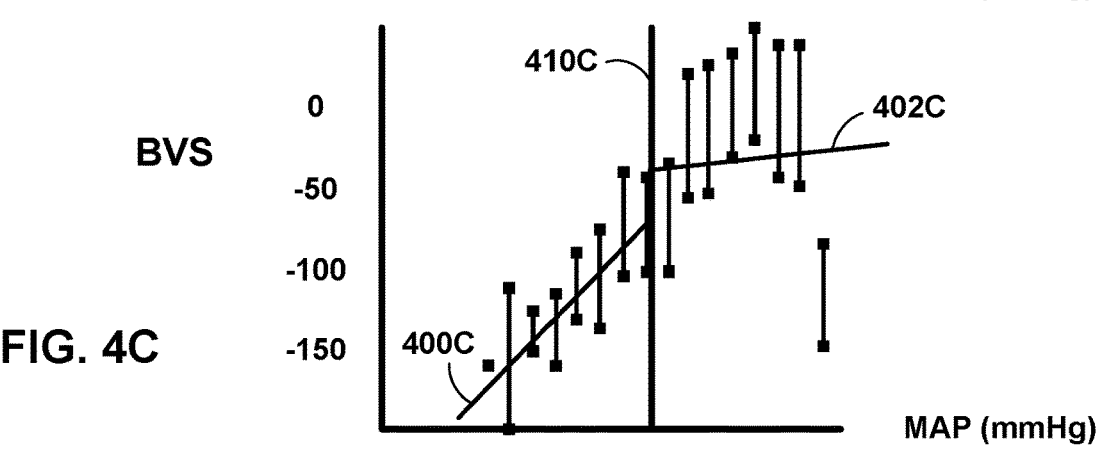
Figure 4D:
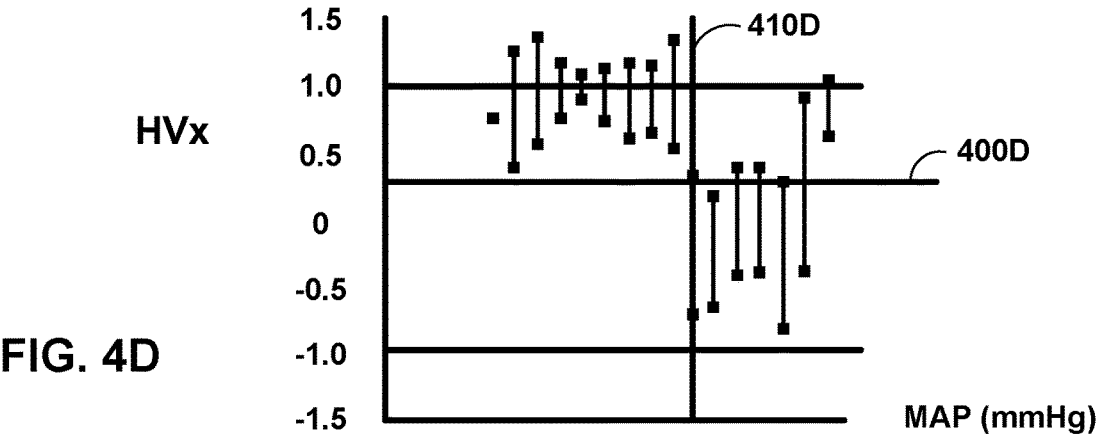
Figure 5:
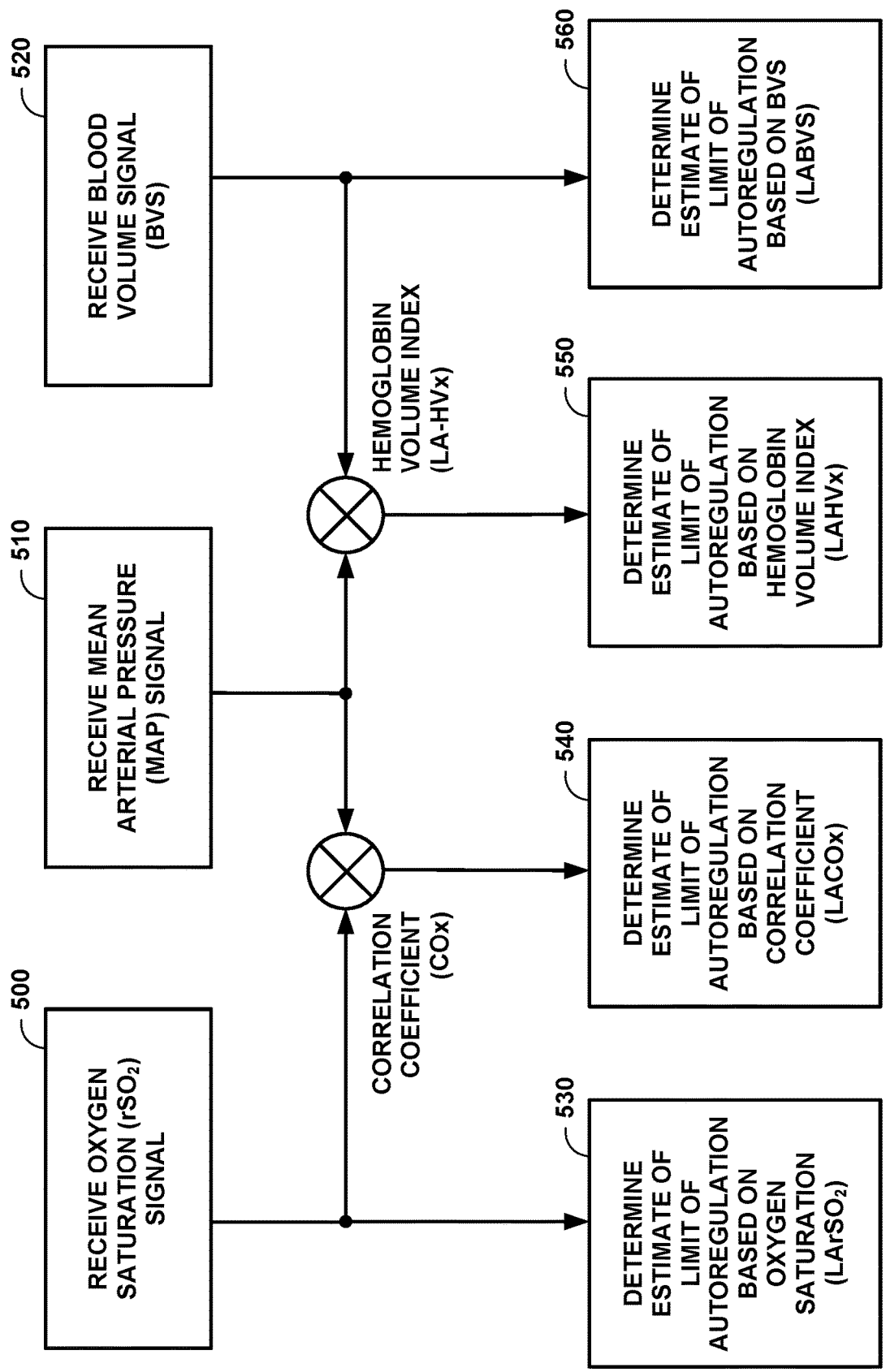
FIG. 5 is a conceptual block diagram illustrating an example framework for determining estimates of a limit of autoregulation.

Processing circuitry 110 may determine estimate 410A of the lower limit of autoregulation based on the oxygen saturation values shown in FIG. 4A. Processing circuitry 110 may determine estimate 410B of the lower limit of autoregulation based on the correlation coefficients shown in FIG. 4B. Processing circuitry 110 may determine estimate 410C of the lower limit of autoregulation based on the blood volume values shown in FIG. 4C. Processing circuitry 110 may determine estimate 410D of the lower limit of autoregulation based on the hemoglobin volume values shown in FIG. 4D. Processing circuitry 110 may be configured to use one of estimates 410A-410D as a "first estimate of the limit of autoregulation" and the remaining one or more of estimates 410A-410D as "other estimates of the limits of autoregulation."

For example, processing circuitry 110 may be configured to determine estimate 410A of the limit of autoregulation based on a set of oxygen saturation values by determining trendlines 400A and 402A. Processing circuitry 110 may determine estimate 410A at the MAP value where the trendlines shift from a positive slope (e.g., trendline 400A) to a negative slope or a near-zero slope (e.g., trendline 402A). Processing circuitry 110 may use a similar technique for determining estimate 410C based on a set of blood volume values. Processing circuitry 110 may determine estimate 410C at the MAP value where the trendlines shift from a positive slope (e.g., trendline 400C) to a negative slope or a near-zero slope (e.g., trendline 402C).

Processing circuitry 110 may be configured to determine estimates 410B and 410D of the limit of autoregulation based on a set of correlation coefficients by determining the MAP values where the mean or median correlation coefficient values are less than or equal to threshold 400B or 400D, respectively. In the example of determining estimate 410B of the lower limit of autoregulation, processing circuitry 110 may be configured to determine the mean or median of COx values for each bin of a plurality of bins, which each bin includes the COx value between two MAP values, such as 50 mmHg and 55 mmHg. Processing circuitry 110 may be configured to determine estimate 410B as the lowest MAP value at which the mean of median of the COx values in a corresponding bin is less than or equal to threshold 400B.

Each of estimates 410A-410D may differ from the other estimates of estimates 410A-410D. Processing circuitry 110 may be configured to determine "the first estimate" of the lower limit of autoregulation as estimate 410A. However, in other examples, processing circuitry 110 may determine "the first estimate" as one of estimates 410B-410D. If processing circuitry 110 determines estimates 410A as the first estimate, then processing circuitry 110 may determine the mean absolute difference between estimate 410A and the mean of estimates 410B-410D, as shown in Equation (1). Processing circuitry 110 may also determine the mean of all four of estimates 410A-410D, as shown in Equation (5). Processing circuitry 110 may then determine a weighting factor for estimate 410A using Equations (8) and (9). Using the weighting factor and a previous value of estimate 410A, processing circuitry can determine a weighted average of estimate 410A and the previous value.

FIG. 5 is a conceptual block diagram illustrating an example framework for determining estimates of a limit of autoregulation. In the example of FIG. 5, processing circuitry 110 receives a first signal indicative of oxygen saturation of a patient (500). Processing circuitry 110 can determine a set of oxygen saturation values based on the first signal. Processing circuitry may then determine an estimate of a limit of autoregulation ($LArSO_2$) based on the set of oxygen saturation values (530).

In the example of FIG. 5, processing circuitry 110 receives a second signal indicative of the MAP of a patient (510). Processing circuitry 110 can determine a set of MAP values based on the second signal and determine a set of COx values based on the set of oxygen saturation values and the set of MAP values. Processing circuitry 110 may then determine an estimate of a limit of autoregulation (LACOx) based on the set of COx values (540).

In the example of FIG. 5, processing circuitry 110 receive a third signal indicative of blood volume of a patient (520). Processing circuitry 110 can determine a set of blood volume values based on the third signal. Processing circuitry 110 may then determine a set of hemoglobin volume index values based on the set of blood volume values and the set of MAP values. Processing circuitry 110 determines an estimate of a limit of autoregulation (LAHVx) based on the set of blood volume values and the set of MAP values (550). Processing circuitry 110 may also determine an estimate of a limit of autoregulation (LABVS) based on the set of blood volume values (560). Processing circuitry 110 may use any of $LArSO_2$, LACOx, LAHVx, or LABVS as the first estimate of the limit of autoregulation.

Figure 6:
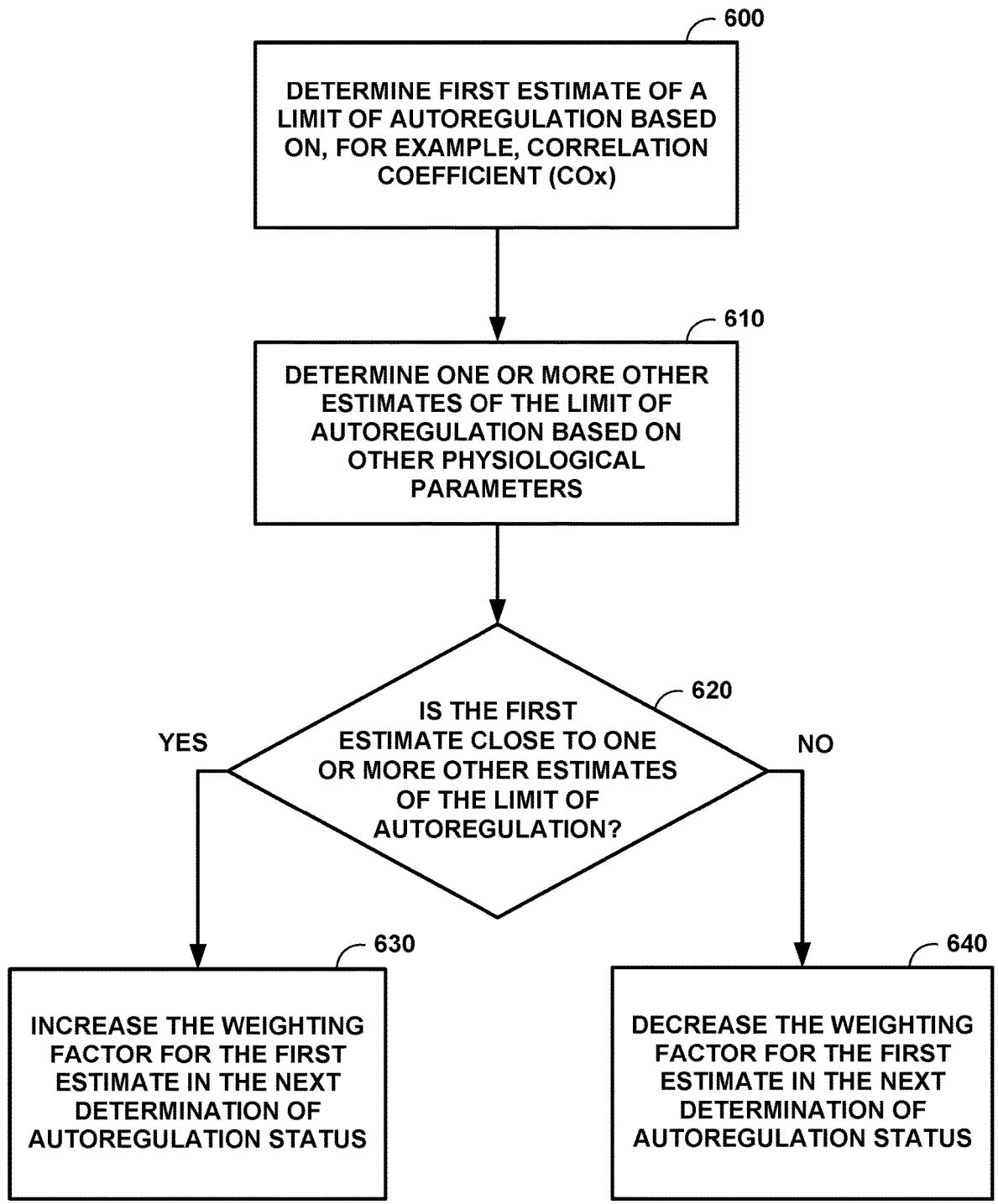
FIGS. 6-8 are flowcharts illustrating example techniques for determining a limit of autoregulation, in accordance with some examples of this disclosure.
Figure 7:
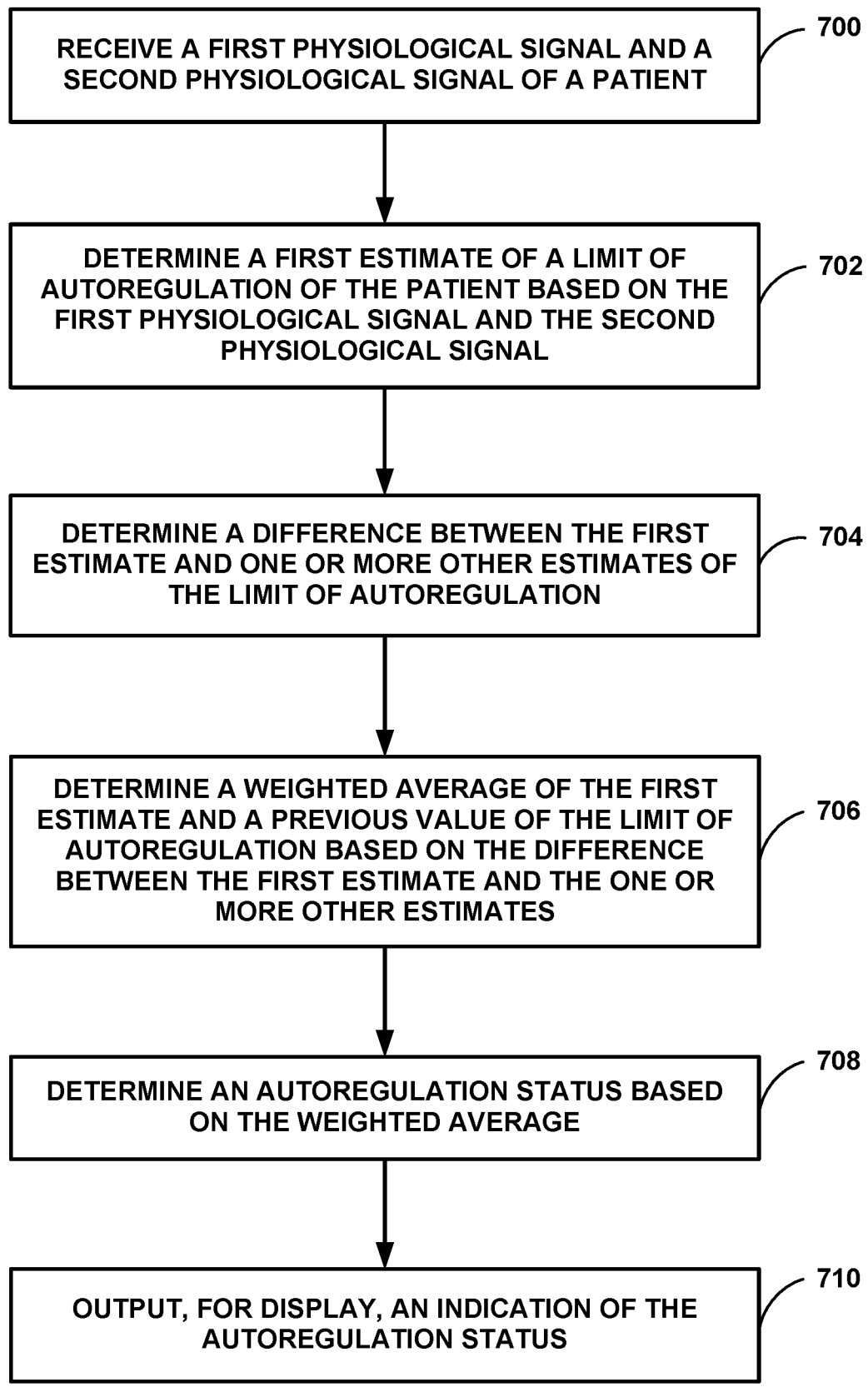
Figure 8:
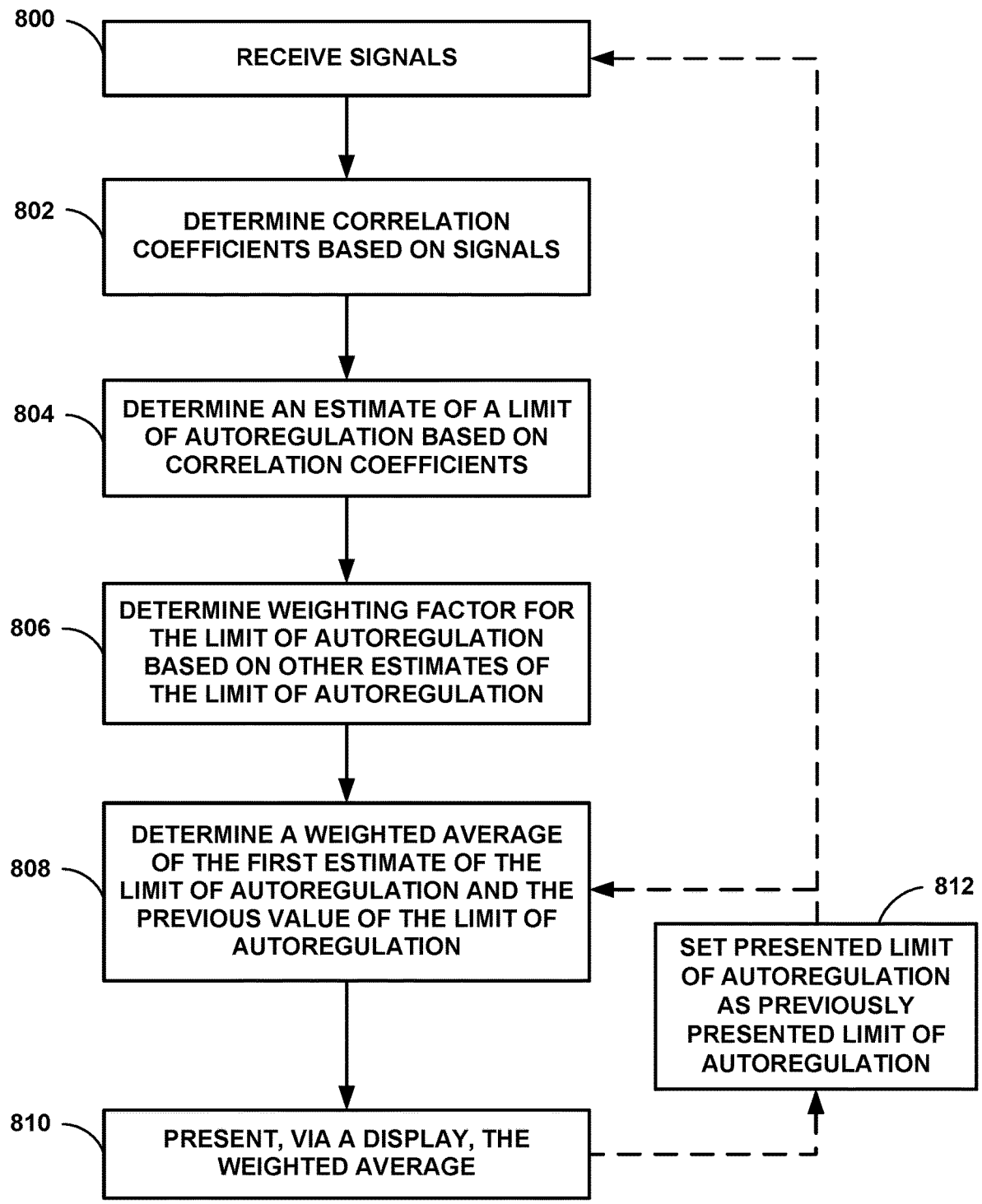

FIGS. 6-8 are flowcharts illustrating example techniques for determining a limit of autoregulation, in accordance with some examples of this disclosure. Although FIGS. 6-8 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 6-8. In the example of FIG. 6, processing circuitry 110 determines a first estimate of a limit of autoregulation based on COx values (600). Processing circuitry 110 also determines one or more other estimates of the limit of autoregulation based on other physiological parameters (610).

In the example of FIG. 6, processing circuitry 110 determines whether the first estimate of the limit of autoregulation is close to the one or more other estimates of the limit of autoregulation (620). If processing circuitry 110 determines that the first estimate is relatively close to the other estimates, then processing circuitry 110 may determine a higher weighting factor for the first estimate, for example, using Equation (9) above or (10) below (630). Relative closeness between the first estimate and the other estimates may indicate a higher likelihood that the first estimate is accurate. The higher weighting factor may increase the effect that the first estimate has on the determination of the weighted average and the autoregulation status by processing circuitry 110. Processing circuitry 110 may determine relative closeness using a normalized difference, for example, shown in Equation (7).

Equation (10) shows an alternative technique for processing circuitry 110 to determine a weighting factor based on a multiplier. Using Equation (10), processing circuitry 110 can determine the weighting factor for the first estimate of the limit of autoregulation by multiplying a predetermined maximum weighting factor by an exponential function of the multiplier. The exponential function of Equation (10), as compared to Equation (9), increases the effect of the multiplier on the determination of the weighting factor.

$$w = w_s \times e^m \quad (10)$$

Equations (11) and (12) show alternative techniques processing circuitry 110 may be configured to use in some examples to determine a multiplier. Using Equations (11) and (12), processing circuitry 110 may reduce the first weighting factor as the difference between the computed parameters increases. In the example of Equation (11), processing circuitry 110 determines a standard deviation of the first estimate of the limit of autoregulation and the other estimates of the limit of autoregulation. Processing circuitry 110 can set the multiplier equal to the standard deviation or to a function of the standard deviation, which can normalize the distance in Equation (1) by the observed variation of all of the estimates. The standard deviation may represent the difference, or the relative closeness, between the first estimate and the other estimates. Processing circuitry 110 can determine a weighting factor based on the standard deviations using Equation (10) or (11).

$$m = \sigma_{LA} = \sqrt{\frac{1}{4}\left[\begin{array}{l}(LACOx - \mu_{LA})^2 + (LArSO_2 - \mu_{LA})^2 + \\ (LAHVx - \mu_{LA})^2 + (LABVS - \mu_{LA})^2\end{array}\right]} \quad (11)$$

$$m = 2 \times \left[1 - \left[1 + \exp\left(-\frac{\sigma_{LA}}{T}\right)\right]^{-1}\right] \quad (12)$$

In the example of Equation (12), processing circuitry 110 determines the multiplier using a normalizing parameter (T) to have a large weight if the other three estimates do not agree. In some examples, where the first estimate is relatively close to the mean of the other estimates, but the other estimates include one or more outliers, the multiplier of Equations (11) and (12) may have a larger value than the multiplier of Equation (8). Thus, processing circuitry 110 can detect the possibility of outlier estimates using Equations (11) and (12) that processing circuitry 110 may not necessarily be able to detect using Equation (8).

In some examples, processing circuitry 110 is configured to determine an autoregulation status for a patient based on the weighted average. Processing circuitry 110 may use the weighted average as an estimate of the limit of autoregulation to determine if a blood pressure or mean arterial pressure of the patient is within an intact region of autoregulation. For example, processing circuitry 110 may use the weighted average as an estimate of the lower limit of autoregulation and determine whether the patient has intact autoregulation by determining whether the mean arterial pressure of the patient is greater than or equal to the weighted average. By determining a weighted average based on a first estimate of the limit of autoregulation and other estimates, processing circuitry 110 may more accurately determine autoregulation status, as compared to another device that does not implement the techniques of this disclosure.

In some examples, processing circuitry 110 can use the following techniques to determine and output a weighted average for determining an autoregulation status. At a first step, processing circuitry 110 determines a first estimate and other estimates of a limit of autoregulation. Processing circuitry 110 can then determine a mean of all of the estimates, for example, using Equation (5). Processing circuitry 110 can also determine a difference between the first estimate and the other estimates, for example, using Equation (1). To determine the difference, processing circuitry 110 can first determine a mean of the other estimates and then subtract the mean of the other estimates from first estimate. In some examples, the difference is an absolute value of the difference of first estimate and the mean of the other estimates.

Processing circuitry 110 may be configured to then determine a normalized difference, for example, using Equation (7) to divide the difference by the mean. Processing circuitry 110 can use the normalized difference to determine a multiplier, as shown in Equation (8). Alternatively, in some examples processing circuitry 110 can use Equation (11) or (12) to determine the multiplier without first determining a normalized difference. Processing circuitry 110 may be configured to determine a weighting factor based on the normalized difference and a maximum predetermined weighting factor, for example, using Equations (9) and (10).

Processing circuitry 110 can use the first weighting factor to determine a weighted value of the first estimate, for example, using Equation (3). Processing circuitry 110 may determine a weighted value by multiplying the first estimate and the first weighting factor. Processing circuitry 110 can also use the first weighting factor to determine a weighted value of the previous value of the limit of autoregulation, for example, using Equation (4). Processing circuitry 110 may determine the weighted value of the previous value by multiplying the previous value and a second weighting factor. Processing circuitry 110 may determine the second weighting factor by subtracting the first weighting factor from one. Thus, both weighting factors may have values between zero and one, and the sum of the weighting factors may be equal to one. Processing circuitry 110 may then determine the weighted average of the weighted value of the first estimate and the weighted value of the other estimates, for example, using Equation (2) to determine a sum of the weighted values. Processing circuitry 110 determines previous value as the previous iteration of the weighted average. Processing circuitry 110 can determine an autoregulation status based on each iteration of the weighted average.

If processing circuitry 110 determines that the first estimate is not relatively close to the other estimates, processing circuitry 110 may determine a lower weighting factor for the first estimate (640). Lack of relative closeness between the first estimate and the other estimates may indicate a lower likelihood that the first estimate is accurate. The lower weighting factor may decrease the effect that the first estimate has on the determination of the weighted average and the autoregulation status by processing circuitry 110. In this manner, processing circuitry 110 can determine a more accurate weighted average by reducing the weighting factor when the estimates of a limit of autoregulation indicate a higher likelihood for error (e.g., when the estimates are not relatively close to each other).

In the example of FIG. 7, processing circuitry 110 receives a first signal and a second signal from sensing circuitry 140 and 141 (700). The signals may be indicative of physiological parameters such as mean arterial pressure, oxygen saturation, and/or blood volume. Processing circuitry 110 then determines a first estimate of the limit of autoregulation based on the first signal and the second signal (702). Processing circuitry 110 also determines one or more other estimates of the limit of autoregulation based on the signals received from sensing circuitry 140-142. Processing circuitry 110 determines a difference between the first estimate of the limit of autoregulation and the one or more estimates of the limit of autoregulation (704). For example, processing circuitry 110 may use Equation (1) to determine a mean absolute difference.

In the example of FIG. 7, processing circuitry 110 determines a weighted average of the first estimate of the limit of autoregulation and a previous value of the limit of autoregulation based on the difference between the first estimate of the limit of autoregulation and the one or more estimates of the limit of autoregulation (706). Processing circuitry 110 can use Equation (2) to determine the weighted average. Processing circuitry 110 can set the previous value of the limit of autoregulation equal to a previous version of the weighted average. Processing circuitry 110 determines an autoregulation status of the patient based on the weighted average (708). Processing circuitry 110 can output, for display by user interface 130, an indication of the autoregulation status. An example of an indication of the autoregulation status is element 350 of graphical user interface 300 shown in FIG. 3.

In the example of FIG. 8, processing circuitry 110 receives or acquires signals from sensing circuitry 140-142 (800) and determines or calculates correlation coefficients (e.g., COx values, HVx values) based on the signals (802). Processing circuitry 110 then determines an estimate of a limit of autoregulation based on the correlation coefficients (804) and determines a weighting factor for the estimate of the limit of autoregulation based on other estimates of the limit of autoregulation (806). Processing circuitry 110 can determine the weighting factor using, e.g., Equations (9) or (10). Processing circuitry 110 determines a weighted average of the first estimate of the limit of autoregulation and a previous value of the limit of autoregulation (808). Processing circuitry 110 may determine the weighted average by adding a calculated LACOx value to a previously reported value in the weighted average (e.g., a previous iteration of the weighted average).

In the example of FIG. 8, processing circuitry 110 presents, via display 132, the weighted average of the first estimate of the limit of autoregulation and the previous value of the limit of autoregulation (810). Processing circuitry 110 may display the new value of LACOx along with an indication of the autoregulation status of the patient. Processing circuitry 110 can then set the weighted average determined during a first iteration as the previous value of the limit of autoregulation for the second iteration of FIG. 8 (812). Thus, during the second iteration of FIG. 8, processing circuitry 110 may use the previous weighted average as the previous value of the limit of autoregulation. Thus, processing circuitry 110 may make the new value of the limit of autoregulation into the next previous value of the limit of autoregulation.

In the second iteration of FIG. 8, processing circuitry 110 receives updated data for the first signal and the second signal (800). Processing circuitry 110 determines an updated first estimate based on the updated data for the first and the second signals (804). Processing circuitry 110 also determines an updated difference between the updated first estimate and other updated estimates. Processing circuitry 110 then determines an updated weighting factor (806) and an updated weighted average of the updated first estimate and the previous value based on the updated difference (808). Processing circuitry 110 determines an updated autoregulation status based on the updated weighted average and outputs, for display, an indication of the updated autoregulation status. Processing circuitry 110 can also present the updated weighted average via display 132 (810).

Processing circuitry 110 may monitor the weighted average to determine if the weighted average is varying significantly over time. Substantial variations in the weighted average over a substantial time duration may indicate that the weighted average is no longer reliable. For example, processing circuitry 110 may determine that the rate of change of the weighted average (e.g., change divided by time) exceeds a threshold rate for at least a threshold time duration. Processing circuitry 110 may store the threshold rate and the threshold time duration to memory 120. In response to determining that the rate of change of the weighted average exceeds the threshold rate for at least the threshold time duration, processing circuitry 110 can cease performing one or more of the following functions: determining the weighted average, determining the autoregulation status, or outputting an indication of the autoregulation status for display.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150-152 and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Where processing circuitry 110 is described herein as determining that a value is less than or equal to another value, this description may also include processing circuitry 110 determining that a value is only less than the other value. Similarly, where processing circuitry 110 is described herein as determining that a value is less than another value, this description may also include processing circuitry 110 determining that a value is less than or equal to the other value. The same properties may also apply to the terms "greater than" and "greater than or equal to."

Various examples of the disclosure have been described. Any combination of the described systems, operations, or functions is contemplated. These and other examples are within the scope of the following claims.

What is claimed is:

1. A device comprising:
a display; and
processing circuitry configured to:
receive a first signal indicative of a first physiological parameter of a patient;
receive a second signal indicative of a second physiological parameter of the patient;
determine a first estimate of a limit of autoregulation of the patient based on the first signal and the second signal;
determine a blood pressure difference between the first estimate of the limit of autoregulation and one or more other estimates of the limit of autoregulation;
determine a weighted average of the first estimate of the limit of autoregulation and a previous value of the limit of autoregulation based on the blood pressure difference between the first estimate of the limit of autoregulation and the one or more other estimates of the limit of autoregulation;
determine an autoregulation status based on the weighted average; and output, for display via the display, an indication of the autoregulation status.

2. The device of claim 1, wherein the processing circuitry is configured to determine the blood pressure difference between the first estimate and the one or more other estimates by at least:
determining a mean of the first estimate of the limit of autoregulation and the one or more other estimates of the limit of autoregulation;
determining a mean absolute blood pressure difference between the first estimate of the limit of autoregulation and a mean of the one or more other estimates of the limit of autoregulation; and
determining a normalized difference by at least dividing the mean absolute blood pressure difference by the mean of the first estimate and the one or more other estimates.

3. The device of claim 2,
wherein the processing circuitry is further configured to determine a multiplier by at least subtracting the normalized difference from one, and
wherein the processing circuitry is configured to determine the weighted average by at least determining a weighting factor for the first estimate of the limit of autoregulation by multiplying a predetermined maximum weighting factor by the multiplier.

4. The device of claim 3, wherein the processing circuitry is further configured to:
determine a new value of the limit of autoregulation based on the weighted average; and
output, for display via the display, an indication of the new value of the limit of autoregulation.

5. The device of claim 1, wherein the processing circuitry is configured to determine the blood pressure difference between the first estimate and the one or more other estimates by at least determining a standard deviation of the first estimate of the limit of autoregulation and the one or more other estimates of the limit of autoregulation,
wherein the processing circuitry is further configured to determine a weighting factor based on the standard deviation of the first estimate and the one or more other estimates, and
wherein the processing circuitry is configured to determine the weighted average of the first estimate of the limit of autoregulation and a previous value of the limit of autoregulation based on the weighting factor.

6. The device of claim 1, wherein the processing circuitry is configured to determine the blood pressure difference between the first estimate and the one or more other estimates by at least:
determining a mean of the one or more other estimates of the limit of autoregulation;
determining a mean absolute blood pressure difference between the first estimate of the limit of autoregulation and the mean of the one or more other estimates; and
determining a normalized difference by at least dividing the mean absolute blood pressure difference by the mean of the first estimate and the one or more other estimates.

7. The device of claim 1, wherein the processing circuitry is configured to determine the weighted average by at least:
determining a first weighting factor and a second weighting factor based on the blood pressure difference between the first estimate of the limit of autoregulation and the one or more other estimates of the limit of autoregulation;
determining a first weighted value of the first estimate of the limit of autoregulation based on the first weighting factor;
determining a second weighted value of the previous value of the limit of autoregulation based on the second weighting factor; and
determining a sum of the first weighted value and the second weighted value.

8. The device of claim 7,
wherein determining the first weighted value comprises multiplying the first weighting factor and the first estimate of the limit of autoregulation, and
wherein determining the second weighting factor comprises subtracting the first weighting factor from one, and
wherein determining the second weighted value comprises multiplying the second weighting factor and the previous value of the limit of autoregulation.

9. The device of claim 1,
wherein the second physiological parameter comprises a blood pressure of the patient,
wherein the processing circuitry is further configured to determine a mean arterial pressure of the patient based on the second signal, and
wherein the processing circuitry is configured to determine the autoregulation status by at least determining whether the mean arterial pressure is greater than or equal to the weighted average.

10. The device of claim 9, wherein the processing circuitry is further configured to:
determine that the mean arterial pressure is less than or equal to the weighted average for more than a predetermined period of time;
generate a notification in response to determining that the mean arterial pressure is less than or equal to the weighted average for more than the predetermined period of time; and
output the notification.

11. The device of claim 1,
wherein the first physiological parameter comprises an oxygen saturation of the patient,
wherein the second physiological parameter comprises a blood pressure of the patient,
wherein the sensing circuitry is further configured to receive a third signal indicative of a blood volume of the patient,
wherein the processing circuitry is configured to determine the one or more other estimates of the limit of autoregulation by at least:
determining a second estimate of the limit of autoregulation based on first signal;
determining a third estimate of the limit of autoregulation based on second signal and the third signal; and
determining a fourth estimate of the limit of autoregulation based on the third signal.

12. The device of claim 11,
wherein the processing circuitry is configured to determine the second estimate by at least determining a set of oxygen saturation values of the patient based on the first signal,
wherein the processing circuitry is configured to determine the third estimate by at least determining a set of hemoglobin volume values of the patient based on the second signal and the third signal, and wherein the processing circuitry is configured to determine the fourth estimate by at least determining a set of blood volume values of the patient based on the third signal.

13. The device of claim 1, wherein the processing circuitry is configured to determine the first estimate by at least:
   determining a set of oxygen saturation values based on the first signal;
   determining a set of mean arterial pressure values based on the second signal;
   determining a set of correlation coefficients based on the set of oxygen saturation values and the set of mean arterial pressure values; and
   determining the first estimate based on the set of correlation coefficients.

14. The device of claim 1, wherein the processing circuitry is configured to determine the first estimate by at least:
   determining a set of blood volume values based on the first signal;
   determining a set of mean arterial pressure values based on the second signal;
   determining a set of correlation coefficients based on the set of blood volume values and the set of mean arterial pressure values; and
   determining the first estimate based on the set of correlation coefficients.

15. The device of claim 1,
   wherein the processing circuitry is further configured to:
   receive updated data for the first signal;
   receive updated data for the second signal;
   set the previous value of the limit of autoregulation equal to the weighted average;
   determine an updated first estimate of the limit of autoregulation of the patient based on the updated data for the first signal and the updated data for the second signal;
   determine an updated blood pressure difference between the updated first estimate and one or more other updated estimates of the limit of autoregulation;
   determine an updated weighted average of the updated first estimate and the previous value based on the updated blood pressure difference;
   determine an updated autoregulation status based on the updated weighted average; and
   output, for display via the display, an indication of the updated autoregulation status.

16. The device of claim 1, further comprising sensing circuitry configured to generate the first and second signals.

17. The device of claim 1, wherein the processing circuitry is further configured to:
   determine that a rate of change of the weighted average exceeds a threshold rate for at least a threshold time duration; and
   cease determining the autoregulation status in response to determining that the rate of change of the weighted average exceeds the threshold rate for at least the threshold time duration.

18. A method comprising:
   receiving, by processing circuitry and from sensing circuitry, a first signal indicative of a first physiological parameter of a patient;
   receiving, by the processing circuitry and from the sensing circuitry, a second signal indicative of a second physiological parameter of the patient;
   determining, by the processing circuitry, a first estimate of a limit of autoregulation of the patient based on the first signal and the second signal;
   determining, by the processing circuitry, a blood pressure difference between the first estimate of the limit of autoregulation and one or more other estimates of the limit of autoregulation;
   determining, by the processing circuitry, a weighted average of the first estimate of the limit of autoregulation and a previous value of the limit of autoregulation based on the blood pressure difference between the first estimate of the limit of autoregulation and the one or more other estimates of the limit of autoregulation;
   determining, by the processing circuitry, an autoregulation status based on the weighted average; and
   outputting, by the processing circuitry for display via the display, an indication of the autoregulation status.

19. A device comprising:
   a display; and
   processing circuitry configured to:
   receive a first signal indicative of a first physiological parameter of a patient;
   receive a second signal indicative of a second physiological parameter of the patient;
   receive a third signal indicative of a third physiological parameter of the patient;
   determine a first estimate of a limit of autoregulation of the patient and two or more other estimates of the limit of autoregulation based on the first signal, the second signal, and the third signal;
   determine a blood pressure difference between the first estimate of the limit of autoregulation and two or more other estimates of the limit of autoregulation;
   determine a weighting factor based on the blood pressure difference between the first estimate and the two or more other estimates;
   determine a weighted average of the first estimate of the limit of autoregulation and a previous value of the limit of autoregulation based on the weighting factor; and
   determine an autoregulation status based on the weighted average.

20. The device of claim 19,
   wherein the processing circuitry is configured to determine the difference between the first estimate and the two or more other estimates by at least:
   determining a mean of the first estimate of the limit of autoregulation and the two or more other estimates of the limit of autoregulation;
   determining a mean absolute blood pressure difference between the first estimate of the limit of autoregulation and a mean of the two or more other estimates of the limit of autoregulation; and
   determining a normalized difference by at least dividing the mean absolute blood pressure difference by the mean of the first estimate and the two or more other estimates,
   wherein the processing circuitry is further configured to determine a multiplier based on the normalized difference, and
   wherein the processing circuitry is configured to determine the weighted average by at least determining a weighting factor for the first estimate of the limit of autoregulation by multiplying a predetermined maximum weighting factor by the multiplier.

* * * * *